US006039945A

United States Patent [19]
Turecek et al.

[11] Patent Number: 6,039,945
[45] Date of Patent: Mar. 21, 2000

[54] PHARMACEUTICAL PREPARATION FOR TREATING BLOOD COAGULATION DISORDERS

[75] Inventors: Peter Turecek, Klosterneuburg/Weidling; Hans-Peter Schwarz; Johann Eibl, both of Vienna, all of Austria

[73] Assignee: Baxter Aktiengesellschaft, Vienna, Austria

[21] Appl. No.: 09/165,745

[22] Filed: Oct. 6, 1998

Related U.S. Application Data

[62] Division of application No. 08/821,763, Mar. 20, 1997, Pat. No. 5,866,122.

[30] Foreign Application Priority Data

| Mar. 20, 1996 | [AT] | Austria | 518/96 |
| Sep. 4, 1996 | [AT] | Austria | 1573/96 |
| Sep. 20, 1996 | [AT] | Austria | 1673/96 |

[51] Int. Cl.[7] .......................... A61K 38/48; A61K 38/00
[52] U.S. Cl. ............................. 424/94.64; 514/2
[58] Field of Search ................. 424/94.64; 514/2

[56] References Cited

U.S. PATENT DOCUMENTS

| 4,287,180 | 9/1981 | Thomas .................... 424/101 |
| 4,382,083 | 5/1983 | Thomas .................... 424/101 |
| 4,395,396 | 7/1983 | Eibl et al. ................. 424/101 |
| 4,501,731 | 2/1985 | Tishkoff et al. ........... 424/101 |
| 4,640,834 | 2/1987 | Eibl et al. ................. 424/94 |
| 4,721,618 | 1/1988 | Giles et al. ............... 514/21 |
| 5,120,537 | 6/1992 | Esmon et al. ............. 514/21 |
| 5,585,259 | 12/1996 | Lauwereys et al. ..... 435/226 |
| 5,593,968 | 1/1997 | Turecek et al. ........... 514/21 |
| 5,618,788 | 4/1997 | Copon et al. ............. 514/12 |
| 5,698,677 | 12/1997 | Eibl et at. ................. 530/381 |
| 5,866,122 | 2/1999 | Turecek et al. ........... 424/94.64 |

FOREIGN PATENT DOCUMENTS

| 0 286 198 A2 | 10/1988 | European Pat. Off. . |
| 0 159 311 B1 | 4/1989 | European Pat. Off. . |
| 0 549 964 A2 | 7/1993 | European Pat. Off. . |
| 0 679 53A | 6/1994 | European Pat. Off. . |
| 350 726 | 6/1979 | Germany . |
| 31 27 318 C2 | 4/1982 | Germany . |
| 382 783 | 4/1987 | Germany . |
| 43 25 872 | 8/1993 | Germany . |

OTHER PUBLICATIONS

Pryzdial et al., Prothrombinase Components can Accelerate Tissue Plasminogen Activator–Catalyzed Plasminogen Activation, J. Biol. Chem. (1995) 270(30) p. 17871–7 (Enclosed is a copy).

Vlasuk et al., "Comparison of the In Vitro Anticoagulant Properties of Standard Herparin and the Highly Selective Factor Xa Inhibitors Antistasin and Tick Anticoagulant Peptide (TAP) in a Rabbit Model of Venus Thrombosis", vol. 65, No. 3, 257–262 (1991).

Drouet et al., "The Effect of Recombinant Human Von Willebrand Factor in Pigs with severe Von Willebrand's Disease", Blood, vol. 86, No. 10, 612a–Abs. No. 2435 (1995).

Raymond et al., "Characterization of the Fawn–Hooded Rat as a Model for Hemostatic Studies", Thrombos. Diathes. haemorrh., vol. 33, 361–369 (1975).

"Parenteral Preparations", Remington's Pharmaceutical Sciences, 15th Edition, Easton: Mack Publishing Co., pp. 1461–1487 (1975).

"Isotonic Solutions", Remington's Pharmaceutical Sciences, 15th Edition, Easton: Mack Publishing Co., pp. 1405–1412 (1975).

Wessler et al., "Biologic assay of a thrombosis–inducing activity in human serum", J. Appl. Physiol., vol. 14, No. 6, 943–946 (1959).

Windholz et al., The Merck Index, 10th Ed., Abstract Nos. 3862–3869, pp. 566–567 (1983).

Hedner et al., "Recombinant Activated Factor VII in thr Treatment of Bleeding Episodes in Patients With Inherited and Acquired Bleeding Disorders", Transfusion Medicine Reviews, vol. 7, No. 2, 78–83 (1993).

Tschopp et al., "Hereditary Defect in Platelet Function in Rats", Blood, vol. 40, No. 2, 217–226 (1972).

Giles et al., "A Canine Model of Hemophillic (Factor VIII:C Deficiency) Bleeding", Blood, vol. 60, No. 3, 727–730 (1982).

Brummelius., "Preparation of the Prothrombin Complex", Methods of Plasma Protein Fractionation, Curling, J.H. ed., 117–128, Acedemic Press, New York (1980).

Fareed et al., "Neutralization of Recombinant Hirudin: Some Practical Considerations", Seminars in Thrombosis and Homeostasis, vol. 17, No. 2, 137–144 (1991).

Fareed et al., "Some Objective Consideration for the Neutralization of the Anticoagulant Actions of Recombinant Hirudin", Haemostasis, vol. 21 (suppl. 1), 64–72 (1991).

Irani et al., "Reversal of Hirudin–Induced Bleeding Diathesis by Prothrombin Complex Concentrate", The American Journal of Cardiology, vol. 75, 422–423 (1995).

*Primary Examiner*—Kevin E. Weddington
*Attorney, Agent, or Firm*—Foley & Lardner

[57] ABSTRACT

There is disclosed a pharmaceutical preparation for treating blood coagulation disorders which comprises purified prothrombinase factors, in particular purified prothrombin and optionally purified factor Xa as active component.

13 Claims, 8 Drawing Sheets

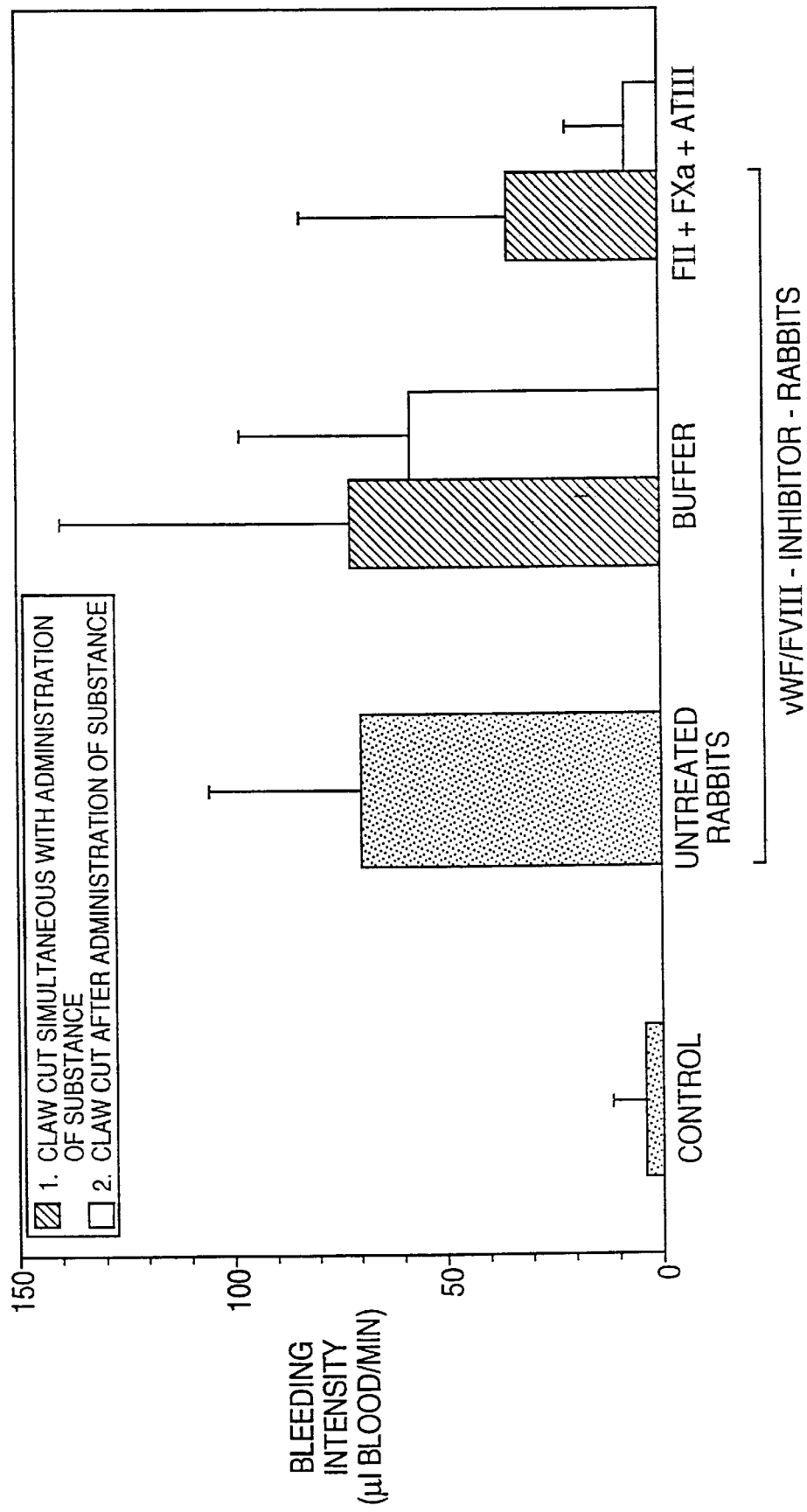

PHARMACEUTICAL PREPARATION FOR TREATING BLOOD COAGULATION DISORDERS

This application is a divisional of application Ser. No. 08/821,763, filed Mar. 20, 1997 now U.S. Pat. No. 5,866, 122.

The present invention relates to a pharmaceutical preparation, in particular for the treatment of blood clotting disorders, comprising coagulation factors which are components of a prothrombinase or of a pro-prothrombinase, respectively.

Prothrombinase is an enzyme substrate complex which forms on a phospholipid surface and enables the activation of prothrombin. By definition, prothrombinase consists of factor II (prothrombin), activated factor X (factor Xa), cofactor V or Va, respectively, phospholipids and calcium ions. In vivo, these factors are present as a transient complex for the activation of prothrombin and the formation of thrombin.

A corresponding pro-prothrombinase is defined as a complex of factors which are present at least partially modified or activated for the formation of a prothrombinase. Pro-prothrombinase thus is to be understood as a proform of a prothrombinase and as complex in which one or more components are present in their pre-stages, as zymogens or as proforms and which is formed on the basis of affinities of the components to one another.

Hemophilia A arises from an X-chromosomal recessive hereditary factor VIII deficiency and becomes manifest by severe blood coagulation disorders. For controlling acute bleedings, coagulation-active plasma protein concentrates are used in most cases, primarily factor VIII concentrates. However, in the classical treatment of hemophilia A-patients with factor VIII preparations, antibodies to factor VIII will form in about 20% of the cases, which antibodies lead to an inhibition of the factor VIII administered with these preparations. One then says that a patient has formed a functional inhibitor to factor VIII and has developed a so-called factor VIII-inhibitor hemophilia or acquired hemophilia.

At present, several methods are used for the therapy of hemophilia A-patients having a factor VIII inhibitor hemophilia:

1.) Treatment with high doses of a factor VIII preparation:

With this, the antibody directed against factor VIII is neutralised in vivo, and the excess of factor VIII can unfold its hemostatic cofactor activity. By repeated administration over an extended period of time, the afflicted patient is desensitized against factor VIII and subsequently in many cases may be subjected to the common factor VIII concentrate therapy. This mode of procedure requires extremely large amounts of factor VIII, is time-consuming and may involve massive anaphylactic side effects at the onset of treatment.

2.) Treatment of factor VIII inhibitor patients with immunoglobulin preparations which contain antiidiotypic factor VIII antibodies:

This route of therapy at present is subject to intensive research. However, no final judgment is as yet possible on the efficacy of such a treatment.

3.) Immunoadsorption:

A further complex method for removing factor VIII inhibitors is the extracorporeal immunoadsorption either on lectins which bind immunoglobulins (protein A, protein G), or on immobilized factor VIII, to which the antibody formed against factor VIII is bound. This method is complicated for the patient because in this case he is bound to an apheresis machine, as with the previous methods it may not lead to a cessation of an acute bleeding and, furthermore, it is expensive.

4.) APCC and derivatives

At present, the therapy of choice is the administration of activated prothrombin complex concentrates (APCC), FEIBA®, AUTOPLEX®, which can be utilized to stop acute bleedings also in patients having high inhibitor titers (cf., e.g., DE-PS 31 27 318 (2)).

Based on the activated prothrombin complex factor concentrates, a component which is also contained in the former, i.e. activated factor VIIa, has been suggested as a therapeutic principle for factor VIII inhibitor patients via the extrinsic coagulation pathway. A corresponding preparation, i.e. recombinant factor VIIa, at present is being clinically tested (Hedner et al., Transfusion Medicine Reviews 7 (2): 78–83 (1993)). Preclinical trials, e.g. on dogs suffering from hemophilia A, have, however, indicated that the treatment with recombinant factor VIIa is ineffective. Similarly, also the success rate in human application is varying. A further disadvantage of recombinant factor VIIa consists in that on account of its very short half-life in vivo, the latter must be administered frequently in high doses per day to control severe bleedings, if possible at all. In such instances it is attempted to administer factor VIIa together with antifibrinolytic agents so as to aid its effect.

In the literature (e.g. DE 44 16 180 A1) it has also been proposed to therapeutically utilize a combination of factor Xa and phospholipids for the treatment of hemophilia A inhibitor patients. In vivo tests on factor VIII-deficient dogs with inhibitor showed that in a suitable dosage such a combination is able to stop an acute bleeding. The therapeutic spectrum of such a preparation is, however, comparatively narrow, since the effective and the thrombogenic dose are closely adjacent, which could, e.g., be demonstrated in rabbits in the Wessler model, since in particular phospholipids constitute an increased thrombogenicity risk.

The present invention thus has as its object to avoid the disadvantages of the methods described and to provide a therapy principle for the treatment of blood clotting disorders, in particular for the treatment of factor VIII inhibitor patients, which enables, i.a., a simple administration, an effective onset of action, an increased half-life and the avoiding of thrombogenic side effects.

According to the invention, this object is achieved with a pharmaceutical preparation for the treatment of blood coagulation disorders comprising, as active components, at least two coagulation factors which are components of a prothrombinase or of a pro-prothrombinase, respectively, in particular with a preparation comprising, as active components, purified prothrombin and purified factor Xa, in the solubilized state, one of the factors besides prothrombin preferably being activated. Preferably, the components are purified at least so far as to be free from endogenous, i.e. starting-material-derived, phospholipids, but also in particular phospholipid vesicles.

Thus, on the one hand, a premature thrombin formation is prevented and the stability of the pharmaceutical preparation is ensured, and, on the other hand, the risk of thromboembolic side effects is minimized.

According to the invention, a mixture or a complex of at least two components of the prothrombinase is understood as a "partial prothrombinase".

Beside the components of the prothrombinase or of the pro-prothrombinase, respectively, advantageously further factors of blood coagulation and fibrinolysis are contained so as to obtain an attenuated effect, in particular an increase, decrease, acceleration or deceleration of hemostasis. Accordingly, activators or pro-activators of blood coagulation, among them factors of intrinsic or extrinsic blood coagulation, can further be contained as zymogens or as activated factors, as well as their agonists or antagonists or inhibitors. Besides, also the corresponding combinations are possible as preparations which are administered separately. Among them are the combination with fibrinogen which above all is suitable for local application.

According to a preferred embodiment, however, the pharmaceutical preparation substantially consists of the "partial prothrombinase", the components of prothrombinase or of pro-prothrombinase, respectively, preferably as a complex. This complex can be purified and treated in a simple manner, in particular treated chemically and/or physically to inactivate molecular, microbial or viral pathogens.

The factors of the pharmaceutical preparations according to the invention are contained in a form which enables activation of at least one factor, or in which at least one factor has already been activated. As factors, preferably human factors are used. The factors are contained in the pharmaceutical preparations according to the invention, which are preferably selected from the group consisting of the factors II, V, Va, X and Xa.

As inventive preparation of a partial prothrombinase or pro-prothrombinase, respectively, preferably combinations of factors II and V or Va, respectively, as well as X and V or Va, respectively, are provided. There, it is particularly preferred that the preparation according to the invention substantially consists of these combinations. Likewise, a pro-prothrombinase comprised of factors II and X, optionally in combination with factor V or Va, respectively, is a preferred embodiment of the present invention.

Therein, native factors can be used, e.g. proteins or their equivalents recovered from plasma or from a plasma fraction, which are, e.g., encoded by recombinant nucleic acids. Furthermore, also respective derivatives which comprise the modified proteins or fragments are also suitable as long as they are activatable or have the respective activity to modulate the generation of thrombin.

The preparation according to the invention has the advantage that, despite its high stability in vitro, it is also stable in vivo until its efficacy is shown by the activation of prothrombin and the generation of thrombin at the site of the wound or of the bleeding. By the contact with the cellular components of the vascular system, e.g. blood cells and vessel walls, in particular phospholipid-containing surfaces, thrombin is generated in situ and hemostasis is promoted. On account of the local efficacy, systemic side effects, such as, e.g., thromboembolic complications, are avoided.

To effect a controlled influence on hemostasis, it is preferred to use highly purified factors which have been purified from interfering contaminants, in particular from a thrombin activity. The factors are especially suitable which have been purified by chromatographic methods, such as ion exchange chromatography, hydrophobic chromatography, affinity chromatography and/or molecular exclusion chromatography. Thereby, specific activities of at least 50% of the theoretic purity, in particular at least 70%, preferably at least 90% up to theoretic purity can be attained for the individual factor. Accordingly it is also preferred to use factors which are substantially free from and devoid of denaturing products and thus are present as purified active factors, enzymes or as activatable zymogens, respectively.

Furthermore, it is preferred to carry out a treatment for the inactivation of infectious pathogens, e.g. by a treatment with chemicals and/or by a physical treatment, such as a heat treatment, radiation or filtration, in particular nanofiltration. According to a preferred variant, the factors of the pharmaceutical preparation according to the invention are treated with detergents, which, on the one hand, leads to the inactivation of viruses and, on the other hand, solubilizes any phospholipids possibly present.

Phospholipids may be contained in preparations of blood coagulation factors, e.g. from plasma or from a plasma fraction or from a cell culture, respectively. The special treatment of the factors for separation of the naturally present phospholipids comprises the solubilisation thereof, on the one hand, and the separation of the phospolipids by the purification methods mentioned above, on the other hand.

Although the preparation according to an embodiment may be utilized in combination with exogenic phospholipids, the preparations according to the invention are preferably free from added phospholipids and contain less than 0.01 mg of phospholipids/U prothrombin. Due to the possible thrombogenic effect of phospholipids, the thrombogenicity risk is further markedly reduced. According to a particularly preferred embodiment, the preparations are free from detectable phospholipid.

According to a further embodiment, the preparation according to the invention furthermore contains magnesium ions. These ions act competitively to calcium ions and can displace the calcium ions in the prothrombinase or pro-prothrombinase, respectively. Thus, a premature thrombin formation in a solution of the preparation according to the invention is prevented and the preparation thus is stabilized to an extent that it remains stable in a solution even for hours.

It has been shown that the pharmaceutical preparation may even be provided as a stable infusion solution, primarily if it is ensured that it does not contain any free calcium ions. For complexing the calcium ions, also a content of a pharmaceutically acceptable chelating agent, e.g. EDTA, and related structures, such as citrate, are suitable.

The preparation according to the invention comprises a biological efficacy in animal models which is comparable to FEIBA® and it can markedly reduce the coagulation time of a factor VIII inhibitor plasma. It can completely normalize the prolonged bleeding time and intensity of bleeding of factor VIII inhibitor rabbits and of von Willebrand factor inhibitor rabbits. By providing purified blood coagulation factors, e.g. purified prothrombin and purified factor Xa, the toxicity of the preparation according to the invention is clearly reduced as compared to FEIB®. Thus, e.g., the effective combination of factor Xa and prothrombin proved negative in the Wessler-thrombosis model (J. Appl. Phys. 14 (1959), 943–946), i.e. for this combination, no thrombogenic effects could be detected in the Wessler model even at higher doses as compared to activated prothrombin complex.

In this thrombogenicity model, rabbits are anesthesized with pentobarbital, whereupon, under an additiional local anesthesia, the vena jugularis is prepared and provided with loose ligatures at a distance of 2 cm. Finally, the substance to be tested is injected within 15 seconds into the ear vein opposite the vena jugularis. After further 25 seconds, the ligatures are closed, and after a waiting time of 10 min the ligatured vein section can be withdrawn and dissected in a Petri dish filled with citrated buffer and evaluated. The evaluation criteria, modified according to Wessler, are as follows: no formation of thrombi=0, a few small thrombi=0.5–1, a few, medium-sized and many small thrombi=2, many medium-sized thrombi=3, a few large thrombi=3.5, one coherent thrombus=4.

The components of the pharmaceutical preparation according to the invention preferably have been purified to such a purity that even at a dose of at least 150 U prothrombin/kg it is free from thromboembolic side effects, expressed by a score in the Wessler thrombosis model of 3 at the most, preferably 2 at the most, in particular less than 2.

In the combination preparation of the invention, prothrombin is contained preferably at a specific activity of at least 5 U/mg protein, more preferred at least 6, in particular at least 7, corresponding to 50, 60 or 70% of the theoretic purity. The factor X or Xa preparation used should preferably have a specific activity of at least 100 U/mg protein, factor Xa preferably being mainly contained as factor Xaβ. Factor V or Va, respectively, is used as co-factor at an approximately equimolar ratio to the coagulation factor of the partial prothrombinase or pro-prothrombinase, respectively. Preferably, the ratio is (0.01–2):1 (mol/mol), most preferably (0.5–2):1.

The preparation used should be as free from thrombin as possible, and it should be possible to detect this freedom from thrombin by suitable, preferably chromogenic, tests (e.g. with the chromogenic substrate TH-1 from IMMUNO AG).

It has been shown that, if the coagulation factors, such as, e.g., prothrombin and factor Xa, are present as a complex in the preparation according to the invention, the preparation has an increased stability as compared to conventional preparations, and the complex furthermore can be subjected to a further treatment for purification and/or inactivation of viruses. In a preferred embodiment of the preparation according to the invention, the preparation further comprises antithrombin III in stabilizing amounts, optionally together with heparin. It is possible to demonstrate also such a preparation's freedom from thromboembolic side effects according to the Wessler test in the absence or also after unmasking of the heparin, i.e. neutralisation and/or separation of the heparin, in a sense that the score of 3 will not be reached.

A complex consisting of at least two coagulation factors which are components of a prothrombinase or of a pro-prothrombinase, respectively, in particular in highly purified form, is of basic importance as a "partial prothrombinase complex". By the presence of calcium ions, such as calcium chloride, the activity of a preparation on the basis of this complex can be accelerated by a multiple. It has also been shown that a preparation comprising this complex and further calcium ions can be used for the preparation of a reagent for diagnostic purposes. A reagent which further comprises thrombin activity and optionally phospholipids is, e.g., suitable to determine factor V cofactor activity. A diagnostic method using this reagent with or without activated protein C, a proteolytic inactivator of factor V, furthermore enables estimation of an extent of an inactivation of factor V or a mutation-caused resistance to activated protein C.

Surprisingly, within the scope of the present invention it has also been found that a pharmaceutical preparation comprising purified prothrombin as the only active component has an effect in vivo comparable to the combination preparation of the invention in the treatment of coagulation disorders, although in vitro with prothrombin alone no shortening of the coagulation time of a factor VIII inhibitor plasma could be achieved.

Thus, a medical indication besides hereditary prothrombin deficiency for a pharmaceutical preparation comprising prothrombin as the only active component has for the first time been shown.

The invention thus also relates to a pharmaceutical preparation, in particular for the treatment of coagulation disorders, comprising purified prothrombin as the only active component.

Preferably, the prothrombin has been purified to such a degree that even at a dose of at least 150 U prothrombin/kg, it is free from thromboembolic side effects, expressed by a score of 3 at the most, preferably 2 at the most, in particular less than 2, in the Wessler thrombosis model.

The combination preparation according to the invention and the prothrombin preparation, respectively, preferably comprise less than 0.1 U of factor VIII:C or of factor VIII:Ag/U of prothrombin, and less than 0.1 U of factor IX/U of prothrombin or less than 0.1 U of factor X/U of prothrombin, respectively. By this, the undesired formation of or reaction with antibodies to these proteins can efficiently be prevented, and the risk of side effects can be reduced.

Although the prothrombin preparation can be used in combination with phospholipids, according to a further preferred variant of the preparations according to the invention, these are free from added phospholipids and contain less than 0.01 mg of phospholipids/U of prothrombin. According to a particularly preferred embodiment, the prothrombin preparations according to the invention are free from detectable phospholipid.

The dosage of the preparations according to the invention is based on the dosage of the equivalent components in FEIBA®. The Factor Eight Inhibitor Bypassing Activity (FEIBA) is defined as that activity of such a preparation which reduces the coagulation time of a factor VIII inhibitor plasma to 50% of the blank value in a clotting test as described in AT 350726. On account of the high purity of the components, the advantages of the preparation according to the invention as compared to FEIBA® reside in a reduced load of plasma proteins on the patient. In particular, the absence of factor VIII:Ag excludes the anaphylactic side effect. Thus it is possible to administer the preparations of the invention at a concentration which provides for a dose which, e.g., comprises at least 50 U prothrombin/kg body weight, this dose for the first time for such preparations being administrable even in a bolus injection because of its freedom from side effects, and thus the otherwise time-consuming administration of such high doses as an infusion can be avoided.

Usually the preparations according to the invention are administered at a dose of e.g. from 50 to 150 U prothrombin/kg body weight, the maximum doses, however, possibly lying far beyond these 150 U/kg body weight (e.g., up to 300 or up to 500, respectively) without possible thromboembolic side effects.

Thus, the invention also relates to administration forms of the pharmaceutical preparations of the invention which comprise a dose of at least 50 U prothrombin/kg body weight, preferably of between 50 and 500 U/kg body weight.

These administration forms may be ampoules or syringes which are already provided for an immediate application, or similar directly or indirectly applicable forms. Among them are containers which are suitable for infusion, intramuscular or subcutaneous application or sets consisting of a container comprising the active agents as a lyophilisate and a container comprising a pharmaceutically acceptable solution suitable for reconstitution of the lyophilisate. Usually, the pharmaceutically acceptable solution or the pharmaceutical preparation, respectively, contains salts, preservatives, buffers and the like in an aqueous solution (cf. Remington's Pharmaceutical Sciences, 15th edition, Easton: Mack Publishing Co., pp. 1405–1412 and 1461–1487 (1975), and The National Formulary XIV., 14th edition, Washington: American Pharmaceutical Association (1975)). Examples of non-aqueous solutions are propylene glycol, polyethylene glycol, vegetable oils and injectable organic esters, such as ethyl oleate. Aqueous carriers are, e.g., water, optionally mixed with alcohol, salt solutions (NaCl), Ringer's dextrose etc. As the preservatives, antimicrobial substances, antioxidants, chelating agents or inert gases may be used.

The preparations according to the invention are also suitable for local treatment, application forms being chosen which become active at the site of a bleeding. Among them are solids or liquids, preferably in the form of a powder, an adhesive tape or a wound cover, respectively, ointments, suppositories, capsules, in particular gastric-juice-resistant capsules, but also drops or sprays.

The coagulation factors used may be both of plasmatic origin and proteins prepared by recombinant DNA technology. What is essential in both instances is that they are present in the pharmaceutical preparation in purified form, in particular in a form freed from endogenous and exogenic phospholipids. Preferably, the pharmaceutical preparations according to the invention are provided in lyophilized form offering the known transportation, storage and application advantages. As the reconstitution solution, a pharmaceutically acceptable solution which optionally comprises ATIII or heparin, respectively, is suitable. Due to the high degree of purity of the components of the preparations according to the invention, they can be reconstituted to an optically clear solution after a short reconstitution time at room temperature, preferably less than 5 min, in particular less than 1 min, with e.g. at least 10 U prothrombin/ml, concentrations of even up to 200 U prothrombin/ml solution being attainable. An optically clear solution is defined by a maximum of the absorbance at 600 nm of 0.1 (for a solution having a protein content of at least 5% by weight, at a layer thickness of 1 cm), based on the pure (buffer) solution as a reference. Alternatively, also a solution having less than 70 light scattering units (LSU), determined by measurement in the nephelometer at 340 nm and a layer thickness of 1 cm is considered to be clear.

In contrast to the hitherto known preparations for treating blood clotting disorders, the preparations according to the invention are extremely stable, i.e. they can be allowed to stand for a longer period of time before being administered. For example, according to the product information, FEIBA® in its ready-to-administer state should not be left to stand for more than 1 hour, whereas the preparations according to the invention as a ready-to-use solution do not exhibit any clotting activation or thrombogenicity even for a period of 3 hours or more at room temperature, and thus the preparations according to the invention may also be provided as infusion solutions which can be administered over a period of several hours. For the same reasons it is also possible to administer the preparations of the invention over an extended period of time as infusion solutions. It has been shown, however, as regards the thromboembolic side effects, there is no substantial difference between a bolus injection and a slow infusion with the preparations according to the invention.

According to a preferred embodiment of the present invention, the pharmaceutical preparations are made available in suitable application devices, preferably as a lyophilisate in syringes which allow for an in situ reconstitution with a pharmaceutically acceptable solution. For the combination preparation an application device is suitable which is shown in FIG. 1, wherein the lyophilisates of prothrombin and factor Xa, e.g., are preferably separately stored and can be administered when required after an in situ reconstitution by means of a double-chamber syringe.

With the pure prothrombin preparation it suffices to provide the prothrombin in a simple syringe, preferably in the lyophilized state, optionally with a pharmaceutically acceptable solution for reconstitution (cf. FIG. 2).

The prothrombin preparation may, however, also be provided as a liquid preparation or in liquid-deep frozen form, respectively.

Particularly if they are recovered from plasmatic proteins or from cell cultures, the pharmaceutical preparations according to the present invention may be subjected to one or several virus inactivation treatments or treatments for virus depletion, respectively, e.g. to a chemical or a chemical-physical treatment, to a heat and/or a detergent treatment according to EP 0 159 311, EP 0 519 901 or EP 0 674 531, or to a physical treatment, such as nanofiltration.

The preparations according to the invention anable a safe and simple treatment of blood coagulation disorders, in which an effective onset of action can be observed within a very short time.

It has been shown that the effective onset of action occurs more rapidly when administering the complex of factor II and factor Xa than with a preparation containing factor II exclusively. To treat a bleeding complication in a patient suffering from inhibitor hemophilia it is, thus, advantageous to treat the bleeding initially by administering the factor II/Xa complex and thus attain a rapid hemostasis and to continue the therapy with maintenance doses of a preparation containing factor II only, to avoid further bleedings.

Furthermore, the long half-life of the preparations according to the invention and their freedom from thrombogenic side effects or the absence of an anaphylactic reaction, which causes an increase in the inhibitor titer, enable a substantially improved treatment of the patient affected with a risk of blood coagulation disorders as compared to known methods. On account of the high concentration or dose of the preparation according to the invention, the patient may receive a depot of the active substance which reduces the need of frequent treatments. The patient may also remain without treatment for a longer period of several days and optionally may treat himself like an outpatient by self-injection, optionally subcutaneously.

The invention further relates to a method of preparing a purified pharmaceutical prothrombin preparation which is characterized in that a prothrombin complex concentrate is subjected to chromatographic purification and the prothrombin-containing fraction is processed to a pharmaceutical preparation. With the method according to the invention a prothrombin preparation is provided which fully meets all the requirements in respect of purity for the pharmaceutical preparations of the invention, in particular as regards the freedom from side effects determined by means of the Wessler test.

In particular, the method according to the invention is characterised by the combination of the following steps:

providing a prothrombin complex preparation in the solid state or as a prothrombin-containing solution, virus inactivation treatment, preferably by heat treatment, in particular in the solid state, optionally dissolving the prothrombin complex preparation, thereby obtaining a prothrombin-containing solution, optionally treating the prothrombin-containing solution with an alkaline earth salt as the solid carrier, prothrombin being adsorbed and subsequently desorbed, optionally concentrating one or several times, preferably by precipitation or ultra/diafiltration, and gel filtration of the prothrombin-containing solution, treating the prothrombin-containing solution with an anion exchanger, the prothrombin being adsorbed and subsequently selectively desorbed, treating the prothrombin-containing solution with a hydrophobic chromatography material, and finishing the prothrombin-containing solution into a pharmaceutical preparation.

Preferably, calcium phosphate, barium sulphate or aluminum hydroxide can be used as the alkaline earth salt. In principle, all anion exchangers which have an affinity to prothormbin can be used as anion exchangers, such as, e.g., DEAE-Sephacel®, DEAE-Sephadext®, DEAE-Sepharose CL6B®, DEAE-Sepharose Fast Flow®, QAE-Sephadex®, Q-Sepharose Fast Flow®, Q-Sepharose High Performance®, Q-Sepharose Big Beads® (all from Pharmacia), DEAE-Tris-Acryl®, DEAE-Spherodexl®, Q-Hyper-D® (all from Sepracor); Macroprep DEAE®, Macroprep Q® (all from BioRad); DEAE-Toyopearl®, QAE-Toyopearl®, Toyopearl Super-Q® (all from Tosohaas), Protein PAK DEAE® (Waters); Fractogel EMD-TMAE®, Fractogel EMD-DEAE®, Fractogel EMD-DMAE®, Licrospher 1000 TMAE®, Licrospher 1000 DEAE® and Licrospher 4000 DMAE® (all from MERCK).

As the gel for the hydrophobic interaction chromatography, preferably Phenyl-Sepharose High Performance® (Pharmacia), yet also other chromatography gels, such as, e.g., Butyl-Sepharose®, Octyl-Sepharose®, Phenyl-Sepharose®, Phenyl-Sepharose Fast Flow High Sub®, Phenyl-Sepharose Fast Flow Low Sub® (all from Pharmacia), Fractogel TSK-Butyl® (MERCK), Macroprep-Methyl-HIC-Support®, Macroprep t-Butyl-HIC-Support® (all from BioRad); TSK-Gel Butyl Toyopear®, TSK-Gel Phenyl Toyopearl® and TSK-Gel Ether Toyopearl® (all from Tosohaas) are used.

A possible embodiment of the method according to the invention is illustrated in FIG. 3.

The prothrombin preparation which can be prepared by the method according to the invention is not only characterised by an extremely high purity which is close to the theoretically possible purity of 10 U/mg, but also by the fact that even at a dosis of at least 150 U of prothrombin/kg it is free from thromboembolic side effects, expressed by a score in the Wessler thrombisis model of 3 at the most, preferably 2 at the most, in particular less than 2, and therebeyond that as a lyophilisate it can be reconstituted with a reconstitution time of 1 min at the most to a clear solution having an activity of at least 10 U of prothrombin/ml up to 200 U of prothrombin/ml. The biological activity of the prothrombin preparation is to be understood as the enzymatic activity obtained upon activation of the prothrombin.

According to a further aspect, the present invention relates to the use of purified prothrombinase factors, in particular of purified prothrombin and, optionally, purified factor Xa, for producing a pharmaceutical preparation for establishing supranormal prothrombin concentrations in a patient's blood, or to establish normal prothrombin concentrations in blood in case of conditions involving a lowered prothrombin level.

It has been shown that with the preparations according to the invention such supranormal factor II levels can be maintained even permanently, i.e. over extended periods of time, which, on the one hand, goes back to the fact that for blood coagulation factors, prothrombin has a very high half-life as a medicament, and, on the other hand, also resides in the fact that the preparations according to the invention are free from side effects so that even a subcutaneous administration, e.g. by depot administration, is possible. The supranormal concentrations of prothrombin which are possible in blood by the administration of purified prothrombin and optionally purified factor Xa or other prothrombinase factors, amount to at least 150%, preferably even at least 200%, corresponding to an activity of at least 1.5 U of prothrombin/ml blood, preferably at least 2.0 to up to 10 U/ml.

Finally, the invention relates also to the use of purified prothrombinase factors, in particular of purified prothrombin and, optionally, purified factor Xa, for preparing a pharmaceutical preparation for the treatment of factor VIII inhibitor conditions, hemophilia A or B, and of von Willebrand Disease. It has been shown that in the animal model, with the preparations according to the invention a rapid and efficient treatment which is free from side effects is possible for all these indications.

Preferably, the preparations according to the invention are provided in a solution having a physiological pH, which preferably does not contain any free calcium ions. However, it is also possible to use an acid buffer in the pH range of from 4.5–6.5, preferably 5–6, which is removed from the factor Xa activity optimum, by which the activation of prothrombin is avoided and therefore the stability of the combination preparation may once more be increased. It goes without saying that all the pharmaceutical additives and solutions suitable for factors II, V, Va, X and Xa may be used for the ready-to-use production of the preparations according to the invention.

Furthermore, it has surprisingly been shown that with the preparations according to the invention even in non-hemophiliacs, acute bleedings, an increased bleeding intensity or an increased risk of bleeding may effectively be treated. In addition to the above-mentioned indications of the various types of hemophilia, i.e. hemophilia A and B as well as inhibitor hemophilia, the preparations according to the invention are also applicable in non-hemophiliacs. Among the non-hemophiliacs there are also those who have blood coagulation disorders based on inhibitors against blood factors which are not factor VIII or factor IX. Furthermore, patients can be treated who exhibit an impaired thrombin generation, which is caused by the absence or functional defect of one or several factors of the extrinsic or intrinsic coagulation or at the formation of antibodies to one or several of these factors or by a lack of the cellular receptor for one or several of these factors. Upon administration of a preparation according to the invention, a coagulation-promoting effect optionally may occur in vivo, whereby a treatment, i.e. a prophylactic or therapeutic administration becomes feasible.

According to a further aspect, the present invention thus relates the the use of at least 2 coagulation factors which are components of a prothrombinase or of a pro-prothrombinase, or to the use of the preparation according to the invention for preparing a pharmaceutical preparation for the treatment of acute bleedings, an increased bleeding insensity or an increased risk of bleeding in non-hemophiliacs.

In particular, conditions can be treated which are caused by an impaired aggregation behavior of blood platelets or thrombopathies, e.g. storage-pool defects, or due to a deficient or dysfunction of platelet-associated proteins, but also bleeding conditions caused by plateles deficiency (thrombocytopenia). One side effect of an anticoagulant therapy resides in the heparin-induced thrombocytopenia, which also constitutes an indication for the preparation acording to the invention.

According to a preferred embodiment, the present invention thus relates to the use of at least 2 coagulation factors which are components of a prothrombinase or of a pro-prothrombinase, respectively, for preparing a pharmaceutical preparation for the treatment of bleedings caused by a thrombocytopenia, in particular for the treatment of a heparin-induced thormbocytopenia.

In this connection it is advantageous that the pharmaceutical preparation prepared according to the method of the invention may have a primary hemostatic activity. The efficacy of the pharmaceutical preparation prepared may be further enhanced by the combination with proteins having primary hemostatic activity. Primarily suited is a von Willebrand factor protein or a fraction of the von Willebrand factor, respectively, with a defined collagen binding activity.

A further indication for the treatment of patients suffering from blood coagulation disorders is the prevention or treatment of bleedings occurring in connection with von Willebrand Disease. This disease with or without a prevalence of coagulation factor inhibitors involves an increased bleeding propensity or a risk of bleeding and in many cases it leads to bleedings which are difficult to control. By aid of the preparation according to the invention it is possible to quickly stop such a bleeding.

Thus, according ot the invention, a set for the treatment of patients suffering from blood coagulation disorders is provided, which comprises the following components:
a) a pharmaceutical preparation comprising at least 2 coagulation factors which are components of a prothrombinase or of a pro-prothrombinase and which are free from phospholipids, and
b) a protein having primary hemostatic activity, in particular vWF.

Bleedings which are difficult to control may in some instances occur as a side effect of a therapy with synthetic, semi-synthetic and biological coagulation inhibitors or anticoagulants or thrombocyte function inhibitors. These substances interfere directly or indirectly with the coagulation system and may disturb the natural coagulation or clotting process in an undesired way. Thus, there is a demand for antagonists for these substances. In the prior art, the use of a prothrombin complex or of a FEIBA® preparation is known for the treatment of bleedings which have been caused by an anticoagulant therapy. In this respect, cf. Irani M. S. et al., The American Journal of Cardiology, Vol. 75, Feb. 15, 1995, p. 422; Fareed J. et al., Haemostasis 1991, Vol. 21 (suppl. 1), pp. 64–72; and Fareed J. et al., Seminars in Thrombosis and Hemostasis 1991, Vol. 17, No. 2, p. 137.

According to a further embodiment of the present invention, the above-stated coagulation factors are used for preparing a pharmaceutical preparation according to the invention for the treatment of bleedings within the scope of an anticoagulant therapy, in particular for preparing a pharmaceutical preparation as an antidote for a coagulation inhibitor or for an anticoagulant or for a thrombocyte function inhibitor. What is substantial is that a risk of thrombosis involved with the presence of phospholipids is avoided. Particularly with patients who are subjected to a therapy with anticoagulants, there is an increased risk of thrombosis. According to the invention, however, the use of phospholipids can be obviated, whereby surprisingly the antidote effect becomes even more specific.

The use according to the invention primarily relates to the antagonizing of a coagulation inhibitor or anticoagulant which indirectly or directly inhibit factor Xa or thrombin. According to the invention, preferably a substance is antagonized which is selected from the group consisting of APAP ((2S)-2-[4-[[(3S)-1-acetimidyl-3-pyrrolidinyl]-oxy]-phenyl]-3-(7-amidino-2-naphthyl)-propionic acid hydro-chloride pentahydrate), benzamidine derivative, hirudin, heparin, heparin analogues, in particular pentasaccharides, AT III heparin complex, AT III, antistasin, "Tick-Anticoagulant Peptide", inactive coagulation factors, in particular "active site"-inhibited coagulation factors, TFPI, competitive ligands for thrombocyte membrane surface receptors, in particular antibodies to GP IIb/IIIa, and their genetically engineered or synthetically produced analogues, in particular peptides, as well as oral anticoagulants. Among the inactive coagulation factors there are primarily derivatised, mutated, fragmented, chemically or physically inactivated or inhibited factors of intrinsic and extrinsic blood coagulation, respectively, which may competitively interact with the native factor.

The antagonizing of a thrombocyte-function inhibitor is primarily indicated in the case of ticlopidin or acetyl salicylic acid.

Acute bleedings are primarily extremely critical in the region of the brain. Therefore, there is a need for the prevention or treatment, respectively, of intracranial bleedings, e.g. intraventricular hemorrhage (IVH). Particularly patients suffering from damaged blood vessels or from an impaired thrombin generation run an increased risk of intracranial bleedings. The preparation according to the ivnention is also specifically suitable for this indication, wherein above all the improved treatment of premature infants becomes possible.

Within the scope of the use according to the invention at the indications listed, the respective kits are each provided which comprise the pharmaceutical preparation of the invention as one component. Furthermore, substances which intensify the hemostatic effect, e.g. a protein having primary hemostatic activity, in particular vWF, may be contained. Besides this, a kit for anticoagulant therapy naturally will contain the respective anticoagulant and the pharmaceutical preparation of the invention as an antidote.

The invention will now be explained in more detail by way of the following Examples and with reference to the associated drawing figures, to which, however, it is not to be restricted.

Therein,

FIGS. 7 and 8 show the in vivo effect of the preparations according to the invention in the von Willebrand factor/factor VIII inhibitor model.

EXAMPLE 1

Figure 1:
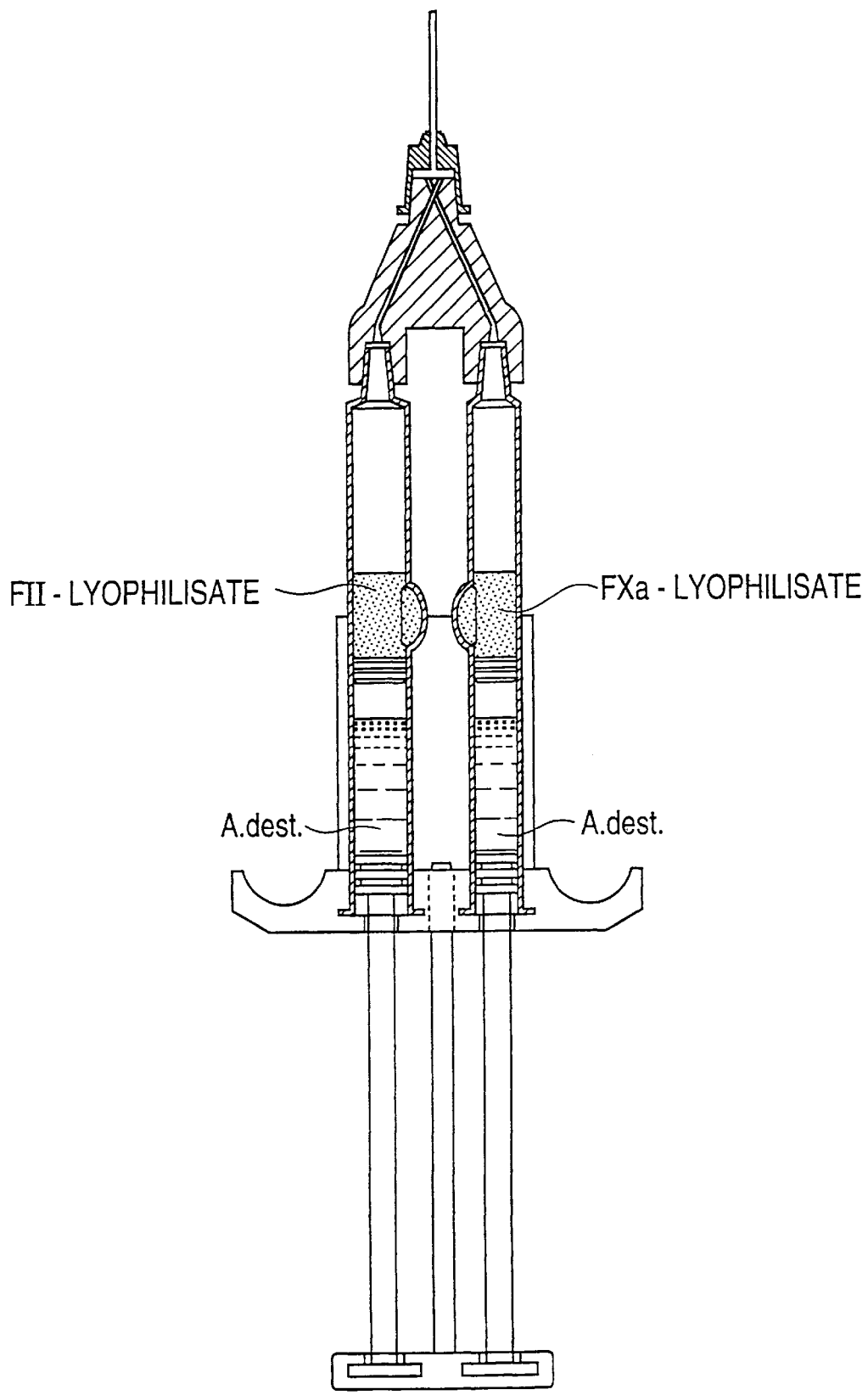
FIGS. 1 and 2 show possible forms of adminstration of the preparations according to the invention.

Preparation of factor X and factor II from a virus-inactivated plasma fraction by means of ion exchange chromatography.

A lyophilized prothrombin complex factor preparation containing factors II, IX, X as well as protein C and protein S was prepared according to the method of Brummelhuis, H. G. J., Preparation of the Prothrombin complex, in Methods of Plasma Protein Fractionation, Curling, J. M. ed., 117–128, Academic Press, New York, (1980), and heat-treated for virus inactivation according to EP 159 311. Accordingly, the lyophilisate (1,000 U of factor X/g, 1,200 U of factor II/g) was dissolved in distilled water so that the latter contained 50,000 U of factor X/l, and adjusted to pH 7.0. After the addition of 12% (v/v) TWEEN® 80 it was stirred for 1 hour at room temperature. Subsequently, it was diluted 1:5 with a 20 mM Tris-HCl-buffer, pH 7.0, and the prothrombin complex protein fraction was adsorbed on calcium phosphate [$Ca_3(PO_4)_2$] at a concentration of 30 g $Ca_3(PO_4)_2$ per l of prothrombin complex solution by stirring for one hour at room temperature. Subsequently, the solid phase was separated by centrifugation at 5,000 rpm for 20 min, and the precipitate was washed twice with 20 mM Tris-HCl-buffer, pH 7.0, containing 10% ammonium sulphate, by resuspension and renewed centrifugation. A third washing was performed in an analogous manner with 20 mM Tris-HCl-buffer, pH 7.0, containing 150 mM NaCl. Elution of the prothrombin complex fraction was performed with 1 M sodium phosphate solution, pH 7.0, wherein 25 ml of this solution per g of calcium phosphate were stirred for 1 hour at room temperature and subsequently the remaining precipitate was separated by centrifugation as above. Subsequently, the supernatant was subjected to an ammonium sulphate precipitation with 366 g of ammonium sulphate per l for 15 h at 4° C. under stirring. The precipitate which contained the prothrombin complex fraction was centrifuged off as above. The precipitate was taken up in a 25 mM trisodium citrate dihydrate buffer, containing 100 mM NaCl, 1 mM benzamidine hydrochloride, pH 6.0, and re-buffered on a column filled with Sephadex® G-25 at 4° C. with a linear flow of 1 cm/min against 25 mM trisodium citrate dihydrate buffer, containing 100 mM NaCl and 1 mM benzamidine hydrochloride, pH 6.0, to separate the ammonium sulfate. Therein, UV absorption at 280 nm and electric conductivity were measured in the eluate flow. The protein-containing fractions were combined and subsequently subjected to an ion exchange chromatography over DEAE-Sepharose FF® (Pharmacia). The fractions were applied to a column (inner diameter:gel bed height=1:1.3) having a gel volume of 8.2 l, 0.55 g of protein/l gel, at a linear flow of 0.36 cm/min. Chromatography was performed at 22° C. Prior to application of the proteins, the column had been equilibrated with a 25 mM trisodium citrate dihydrate buffer, containing 100 mM NaCl, 1 mM benzamidine hydrochloride, pH 6.0. Elution of the protein fraction was effected in several stages with a buffer 1 (25 mM trisodium citrate dihydrate, 1 mM benzamidine hydrochloride, 245 mM NaCl, pH 6.0), a buffer 2 (25 mM trisodium citrate dihydrate, 1 mM benzamidine hydrochloride, 270 mM NaCl, pH 6.0), and a buffer 3 (25 mM trisodium citrate dihydrate, 1 mM benzamidine hydrochloride, 400 mM NaCl, pH 6.0). Elution with buffer 1 was carried out with 2.4 column volumes, inert protein being separated therewith. Elution with buffer 2 was carried out with 5.6 column volumes, and there fractions were collected which were analysed for their contents of factor II, factor X, protein C and factor IX. The factor X-containing fractions which were free from factor II, IX and protein C, were combined. By elution with buffer 3 (1.9 column volumes), factor II was desorbed, wherein again fractions were collected and assayed for their contents of factor X, factor IX and factor II. The factor II-containing fractions were pooled. Both, factor II and the factor X-containing pool optionally could be subjected to an additional treatment for inactivation of pathogenic impurities by the addition of 1 M KSCN and incubation at 22° C. for several hours.

EXAMPLE 2

Purification of factor II by means of hydrophobic interaction chromatography

The factor II pool recovered in Example 1 was adjusted to 1.8 M NaCl by the addition of sodium chloride, and the pH was corrected to pH 7.0. Subsequently, this solution was adsorbed to a gel, Phenylsepharose High Performance® (Pharmacia), by hydrophobic interaction, wherein 3 g of protein/l gel were bound. In a column having a ratio of inner diameter:gel bed height=1:1.9, the protein fraction was adsorbed at a linear flow of 0.25 cm/min, and subsequently freed from inert protein by washing with a buffer (25 mM Tris-HCl, 3 M NaCl, pH 7.4). Factor II was eluted from the column by gradient elution with 11.5 column volumes of 3 M–0.9 M NaCl with simultaneous collection of fractions, and those fractions which contained factor II activity but were free from factor X and factor IX, were pooled. Subsequently, the collected factor II fractions were concentrated ten-fold by ultra/diafiltration via an ultrafiltration membran having a cut-off of 30 kD, and re-buffered against a buffer containing 4 g of trisodium citrate dihydrate/l, 8 g NaCl/l, pH 7.0. A thus prepared factor II preparation had a specific activity of 6.9 U/mg protein. The determination of the factor II activity was effected with the 1-stage method based on the thromboplastin time, by using a factor II-deficient plasma against the international factor II standard by using the reagent combination from IMMUNO, Vienna. In clotting analyses, other coagulation factors were detectable in traces or not at all (factor VII<0.00002 U/U factor II, factor IX 0.0002 U/U factor II, factor X 0.004 U/U factor II, protein C 0.003 U/U factor II, and factor VIII<0.0002 U/U factor II).

EXAMPLE 3

Purification of factor II by means of hydrophobic interaction chromatography and hydroxyl apatite chromatography As an alternative preparation method for a highly purified factor II also a method was used, in which at first factor IX was separated from a lyophilized prothrombin complex factor preparation (cf. Example 1) by hydrophobic chromatography, subsequently factor II was isolated, and the latter was then highly purified by chromatography on hydroxyl apatite. The prothrombin complex factor preparation was dissolvd as in Exmaple 1 and incubated with a detergent at room temperature for 1 h. Subsequently, a factor II, IX and X-containing fraction was isolated as in Example 1 by ion exchange chromatography on DEAE-Sepharose FF® (Pharmacia). From this, the factor IX-containing fraction was subsequently removed by interaction with Butyl-Toyopearl® (Toso Haas). Subsequently, the adsorption supernatant was purified by a further hydrophobic interaction chormatography on Phenyl-Sepharose High Performance® (Pharmacia), wherein approximately 4 g of protein/l gel could be adsorbed. In a column having a ratio of inner diamter:gel bed height=1:1.9, the protein fraction was adsorbed at a linear flow of 0.25 cm/min, subsequently the inert protein was removed by washing with 20 mM Tris-HCl, 3 M NaCl, pH 7.4, and finally the factor II-containing fraction was isolated by step-wise elution which desorbed from gel with decreasing conductivity at 1.9 M NaCl. The factor II-containing fraction was then directly adsorbed on Ceramik-Hydroxylapatite® (Biorad). This was carried out on a column having a ratio of inner diameter:gel bed height=1:4.8. Elution was done at a linear flow of 3 cm/min. By elution with a salt gradient, factor II could be desorbed from the column. The factor II-containing fractions were collected and concentrated via ultra/diafiltration over polysulfon membranes with a cut-off of 30 kD, until the factor II concentration was 50–100 U/ml. A thus prepared factor II preparation had a specific activity of at least 7 U/mg protein. Other coagulation factors, in particular factor IX and factor VIII, were detectable only in traces or not at all, as in the preparation from Example 2. By selection of a suitable diafiltration buffer, the factor II preparation was transferred into a pharmaceutically compatible buffer (e.g. 4 g of trisodium citrate dihydrate/l, 8 g NaCl/l, pH 7.0).

EXAMPLE 4

Recovery of factor Xa

The factor X fraction prepared as described in Example 1 subsequently was further processed to factor Xab as described in DE 43 25 872, wherein the thus-obtained highly purified factor Xa preparation was lyophilized in the presence of 1 g/100 ml human albumin. Such a preparation was free from other clotting factors; the contained factor Xa had a specific activity of 120 U/mg protein before the addition to albumin.

EXAMPLE 5

Lyophilization of factor II

The preparation containing highy purified factor II described in Example 3 was lyophilized without the addition of stabilizers, more than 80% of the initial activity remaining after lyophilization.

EXAMPLE 6

Colyophilization of factor II and factor Xa

A factor II preparation prepared according to Example 3 was filled at a concentration of 100 U/ml at 20 ml into 50 ml bottles and shock-frozen at −80° C. Subsequently, a solution of a highly purified factor Xa which had been prepared according to DE 43 25 852 and had a concentration of 500 U/ml was dosed in an amount of 30 μl onto the frozen factor II solution. By immediate freezing of the small volume, a mixing of the factor II and factor Xa phases was prevented. Subsequently, it was lyophilized. To prepare the infusion solution, the lyophilzate was reconstituted with 20 ml A. dest., mixed, and immediately prepared for administration.

EXAMPLE 7

Pharmaceutical formulation of factor II, factor Xa and antithrombin III and/or antithrombin III heparin complex The highly purified factor II in combination with factor Xa and antithrombin III or antithrombin III heparin complex were diluted to the application concentration in a buffer containing 4 g of trisodium citrate dihydrate/l and 8 g NaCl/l, pH 7.0. These solutions could be lyophilized, an activity of at least 80% of the respective components remaining.

EXAMPLE 8

Detection of partial prothrombinase

Figure 4:
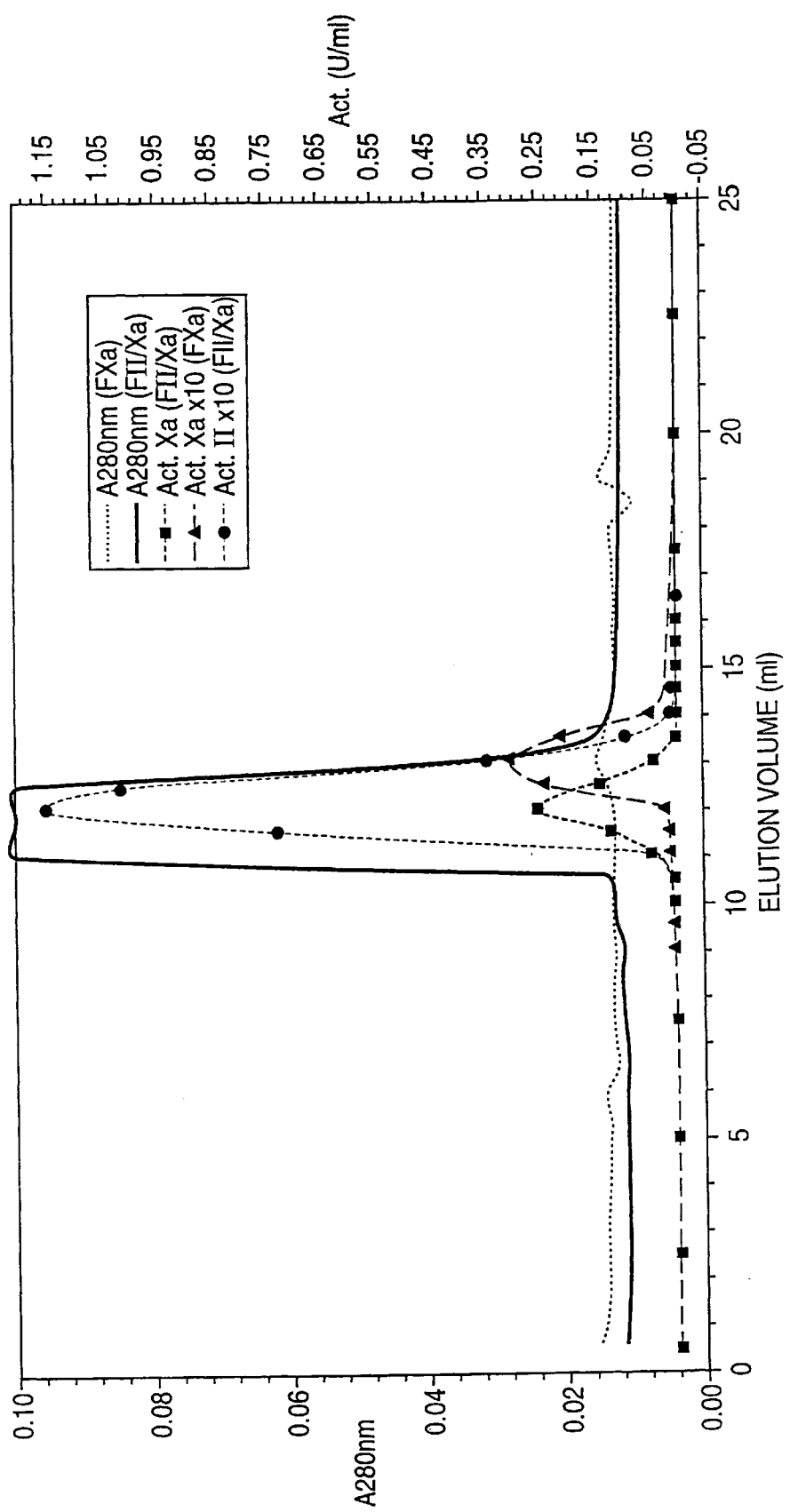
FIG. 4 shows the demonstration of the partial prothrombinase complex.

Formation of a complex of factor II and factor Xa to "partial prothrombinase" was demonstrated by the following experiment:
57 U of factor II from Example 3 and 1.2 U of factor Xa from Example 4 were dissolved in 20 mM Tris-HCl buffer, containing 150 mM NaCl, pH 7.4, and incubated for 15 min at room temperature for the formation of the complex. Subsequently, one aliquot of the solution was chromatographed by gel permeation chromatography over Superose® 12 (HR10/30) (Pharmacia) at a flow rate of 0.25 ml/min. The application volume was 200 μl. The throughput through the column was measured UV-spectrophotometrically at 280 nm and collected in fractions of 0.5 ml. Subsequently, factor Xa which was determined with a chromogenic substrate in a photometric test by means of the method described in DE 43 25 872 was measured quantitatively in the fractions. Likewise, the factor II activity was determined in the individual fractions as in Example 2. The result can be taken from FIG. 4. Factor Xa [FIG. 4: - -■- - Act. Xa (FII/Xa)] and factor II [FIG. 4: - -●- - Act. II x 10(FII/Xa)] eluted together with the protein fraction [FIG. 4: — A280 nm (FII/Xa)]. Under identical conditions, factor Xa then was applied alone to the column, the elution profile was determined after gel passage by measureing the UV absorption at 280 nm [FIG. 4: .......A280 nM (FXa)] and factor Xa activity [FIG. 4: - -▲- - Act.Xa×10 (FXa)] was determined in the fractions. The protein peak corresponding to factor Xa was clearly offset from factor Xa in the complex with factor II. By reducing the retention time of factor Xa in the complex on the column and together therewith for displacement to an apparently higher molecular mass, it was possible to proove a complex formation of factor II and factor Xa (partial prothrombinase).

EXAMPLE 9

Formulation of the preparation in the double chamber syringe system

To simplify the application of the multiple-component system, such as, e.g., mixtures of factor II and factor Xa or factor II, factor Xa and antithrombin III, a double double-chamber syringe body, as described in AT 382 783, can be used as application device. In the clinical application of lyophilized multiple-component systems, the latter would otherwise each have to be reconstituted and mixed with each other at a defined ratio before being administered to the patient. Filling of the corresponding lyophilisate into a double-chamber syringe system allows for an exact dosing to a pre-determinable activity of the preparation for the treatment of inhibitor hemophilia, e.g. to conventional FEIBA units, which can be determined according to AT 350 726. By using such a system, the effective mixture is prepared in situ at the injection. In one embodiment, lyophilisates of the active substances, factor II and factor Xa, are each present in the two double-chamber syringe bodies, which, on account of the ready solubility of the highly purified proteins, solubilize at once and are immediately infused into the patient by further pressing down the syringe piston after mixing in the mixing head (cf. FIG. 1).

Figure 2:
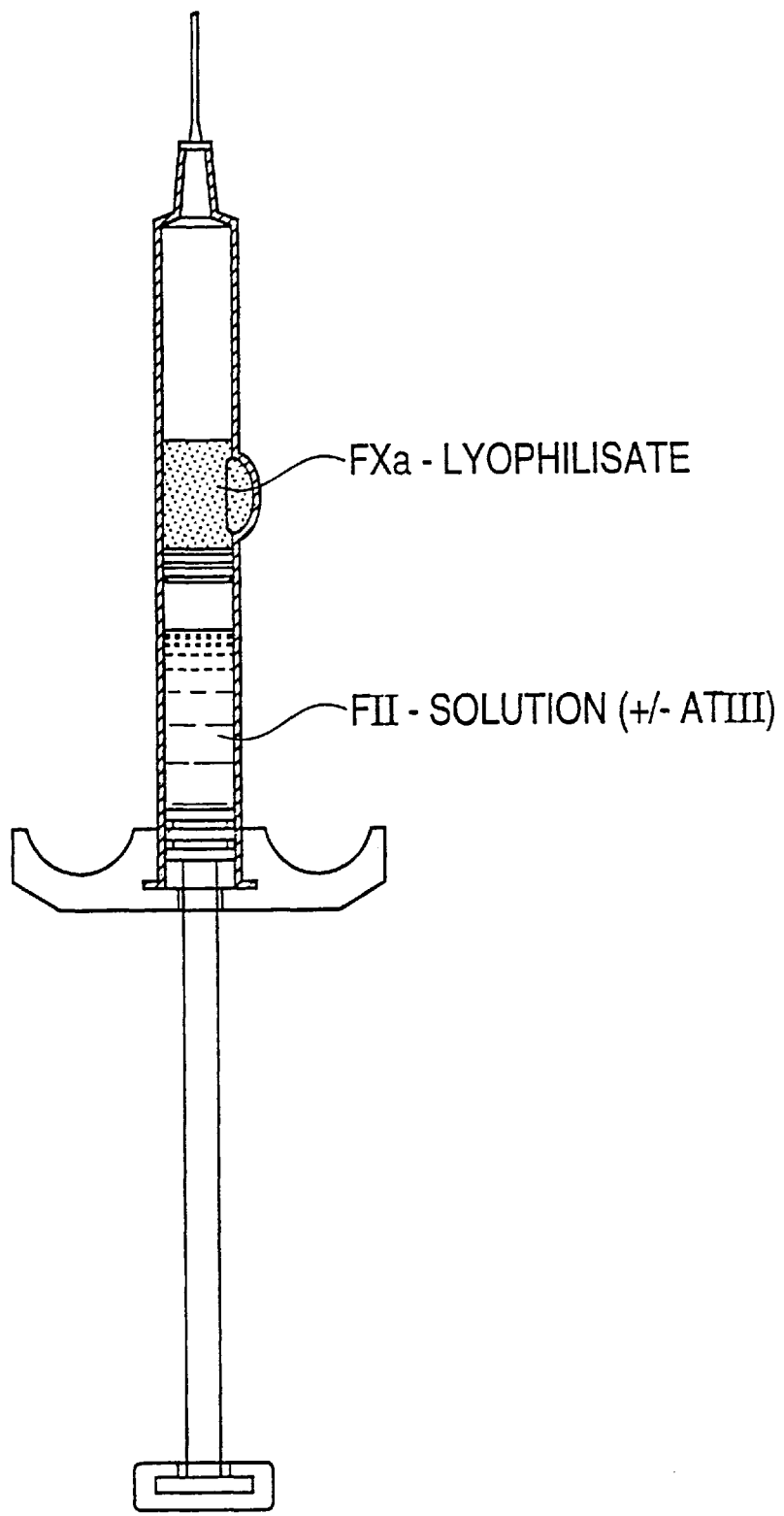
Figure 3:
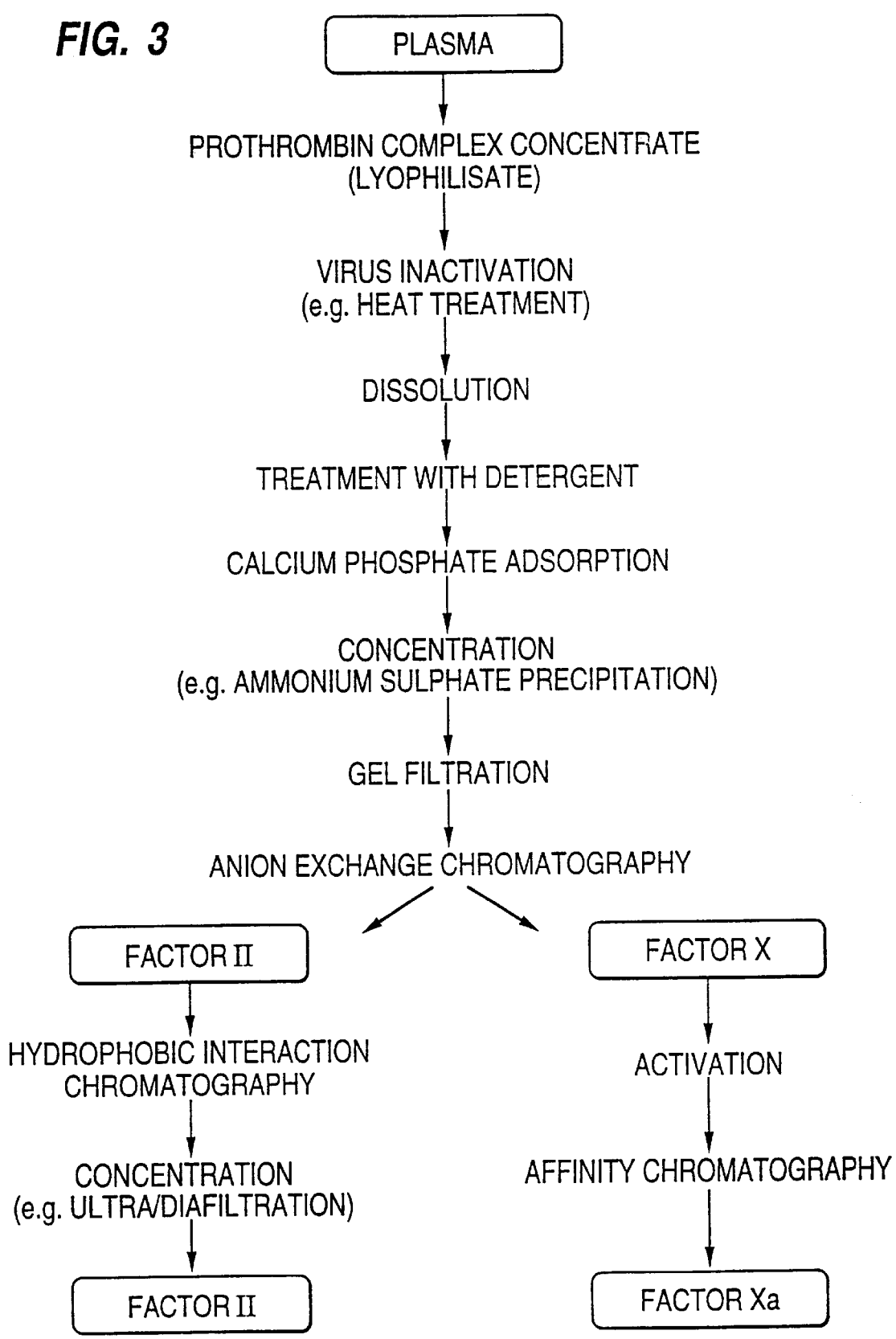
FIG. 3 shows the flow diagram of one embodiment of the preparation method.

On account of the high stability of factor II in solution, the former also is suitable as a solvent for factor Xa in the application form of a double-chamber syringe. A solution of highly purified factor II, prepared e.g. according to Example 2, in a physiologically compatible citrate buffer (4 g of trisodium citrate dihydrate/l, 8 g NaCl/l, pH 7.0) at a concentration of 100 U factor II/ml, is admixed with antithrombin III (IMMUNO, Vienna) (1 mU antithrombin III/U factor II). This solution is used as a solvent for the lyophilized powder of a highly purified factor Xa in a double-chamber syringe (cf. FIG. 2).

EXAMPLE 10

Stability of the highly purified factor II

Factor II was purified as described in Example 2 and stored as a solution at a concentration of 60 U/ml in a buffer containing 4 g/l trisodium citrate dihydrate, 8 g/l NaCl, pH 7.0, at 5° C., at 22° C., at 37° C. and at 50° C. At the storage temperatures of 5° C. and 22° C., samples were drawn every 24 h, at the storage temperatures of 37° C. and 50° C., samples were taken over 24 h at 1 h, 2 h, 4 h, 8 h and 24 h. In each sample the factor II activity was determined.

At 5° C. more than 80% of the initial activity could be detected even 86 days after storage had been started. At 22° C., more than 80% of the initial activity was found for 14 days; at 37° C., 95% of the initial activitiy could be found 24 h after storage had been started. Even at 50° C., 94% of the original activity could still be found 8 h after storage had been started.

EXAMPLE 11

Autoactivation and stability of the preparations according to the invention

Inventive preparations according to Example 5 (factor II) and Example 6 (factor II/Xa complex) were examined in an in vitro-test for their prothrombotic properties particularly of the extrinsic clotting system, as compared to two commercially available prothrombin complex concentrates. Before being used in the test, the heparin present in the prothrombin complex concentrate was neutralized with protamin sulphate corresponding to the concentration (of heparin) so as to exhibit thrombogenic substances that would be masked by heparin.

The analysis material consisted of 250 μl Thrombotest® (Nycomed Pharma AS, Oslo, Norway), a preparation containing thromboplastin from bovine brain and adsorbed bovine plasma, which was pre-incubated for 3 min at 37° C. Subsequently, 50 μl of a sample were added, and the clotting time was determined by means of a spherical coagulometer (KC4, Amelung). Bovine thromboplastines are considered to be particularly sentitive to activated clotting factors. Accordingly, the test system can provide information on the in vitro-thrombogenicity of the preparations assayed. In this test, undiluted normal human plasma was used as a control. The latter had a clotting time of 74 seconds. When used undiluted, the two assayed preparations of the invention had clotting times of more than 100 seconds, the concentration corresponding to a possible application concentration of 30 U of factor II/ml. E commercially available prothrombin complex concentrate, likewise dissolved in the application concentration and diluted to 30 U/ml, had to be further diluted with buffer 1: 32 to achieve the clotting time of normal plasma (74 seconds). A further commercially available, activated prothrombin complex concentrate even had to be diluted with buffer 1: 216 so as to achieve the clotting time of normal plasma, i.e. 74 seconds. Subsequently, the preparations according to the invention were stored in the dissolved state at room temperature for up to 4 h and samples were taken once per hour, and again the clotting time was determined by means of Thrombotest®. No change had taken place, i.e. even after 4 h the samples used in the undiluted state still have clotting times of more than 100 seconds. From these tests it could be seen that the preparations according to the invention have a markedly lower thrombogenicity potential as compared to commercially available prothrombin complex concentrates.

EXAMPLE 12

Dissolution behavior of the preparation according to the invention

A highly purified factor II-containing preparation was prepared as described in Example 5 and lyophilized. The lyophilisate was adjusted such that the volume activity was 50 U/ml after reconstitution with distilled water. This was a typical application concentration. On account of the high purity of the preparation, however, also volume concentrations of 100 and more units of factor II per ml could be achieved. The dissolution time of the preparation, defined as that time which passes from the addition of the solvent (distilled water) until the complete dissolution of the powder was determined. In comparison thereto, the lyophilisates of two commercially available preparations, i.e. prothrombin complex and activated prothrombin complex, were each reconstituted according to the supplier's instruction at the application concentration by the addition of distilled water, and the dissolution times were also determined. The dissolution times of the tested preparations can be taken from the following table:

| | Preparation of the invention | APCC[1] | PCC[2] |
|---|---|---|---|
| Dissolution time (s) | <30 | 240 | 300 |

[1]APCC=activated prothrombin complex concentrate
[2]PCC=prothrombin complex concentrate When the respective preparations had been dissolved, an UV/VIS spectrum between 280 and 750 nm was measured of each of them, against a citrated saline buffer. The spectra can be taken from FIGS. 5a, b and c (a: preparation according to the invention; b: activated prothrombin complex; c: prothrombin complex). A comparison of the specta showed that the preparation according to the invention had a markedly lower light absorption in the visible range up to 700 nm than the preparations of comparison. The preparation according to the invention thus was marked by an excellent solubility and, in the dissolved state, was present as a clear, uncolored solution, as is characteristic of an improved pharmaceutical preparation.

EXAMPLE 13

Effect of the preparation in factor VIII inhibitor plasma

A high-titer factor VIII inhibitor plasma (55 BU/ml) was pre-cooled in an ice bath and incubated for one minute and at 37° C. with PTT reagent (IMMUNO, Vienna) and the sample to be tested, both also pre-cooled in an ice bath, at a ratio of 1+1+1. Subsequently, 1 part of an 0.05 M $CaCl_2$ solution was added, and the clotting time of the test mixture was determined by means of a spherical coagulometer (Amelung), model KC-4. The preparations to be tested were further diluted 1:10 in a buffer comprising 7 g NaCl/l and 6 g of trisodium citrate dihydrate/l, and used for the test at this concentration. Under these conditions, highly purified factor II, alone and in combination with highly purified factor Xa, in combination with antithrombin III and heparin was tested. The clotting times can be taken from the following table.

| Test substance (concentration) | | | | Clotting |
|---|---|---|---|---|
| Factor II | Factor Xa | Antithrombin III | Heparin | time (sec) |
| 10 U/ml | — | — | — | 147 |
| 10 U/ml | 0.1 U/ml | — | — | 63 |
| 10 U/ml | 0.1 U/ml | 1 U/ml | — | 55 |
| 10 U/ml | 0.1 U/ml | 1 U/ml | 6 U/ml | 49 |

As the control, the clotting time of the test sample was determined with pure sodium chloride trisodium citrate buffer. The latter was 148 seconds. Thus, the clotting time of the inhibitor plasma could be markedly reduced merely by the addition of factor II/Xa with or without antithrombin III or heparin. By measuring a FEIBA standard preparation (FEIBA STIM 4, IMMUNO), which is the conventional preparation for the treatment of factor VIII inhibitor patients, at various concentrations in the same test sample it could be found that the FEIB-activity of the preparation containing 10 U/ml factor II and 0.1 U factor Xa/ml corresponds to approximately 25 U FEIBA/ml.

EXAMPLE 14

In vivo-effect with factor VIII inhibitor hemophilia

Figure 6:
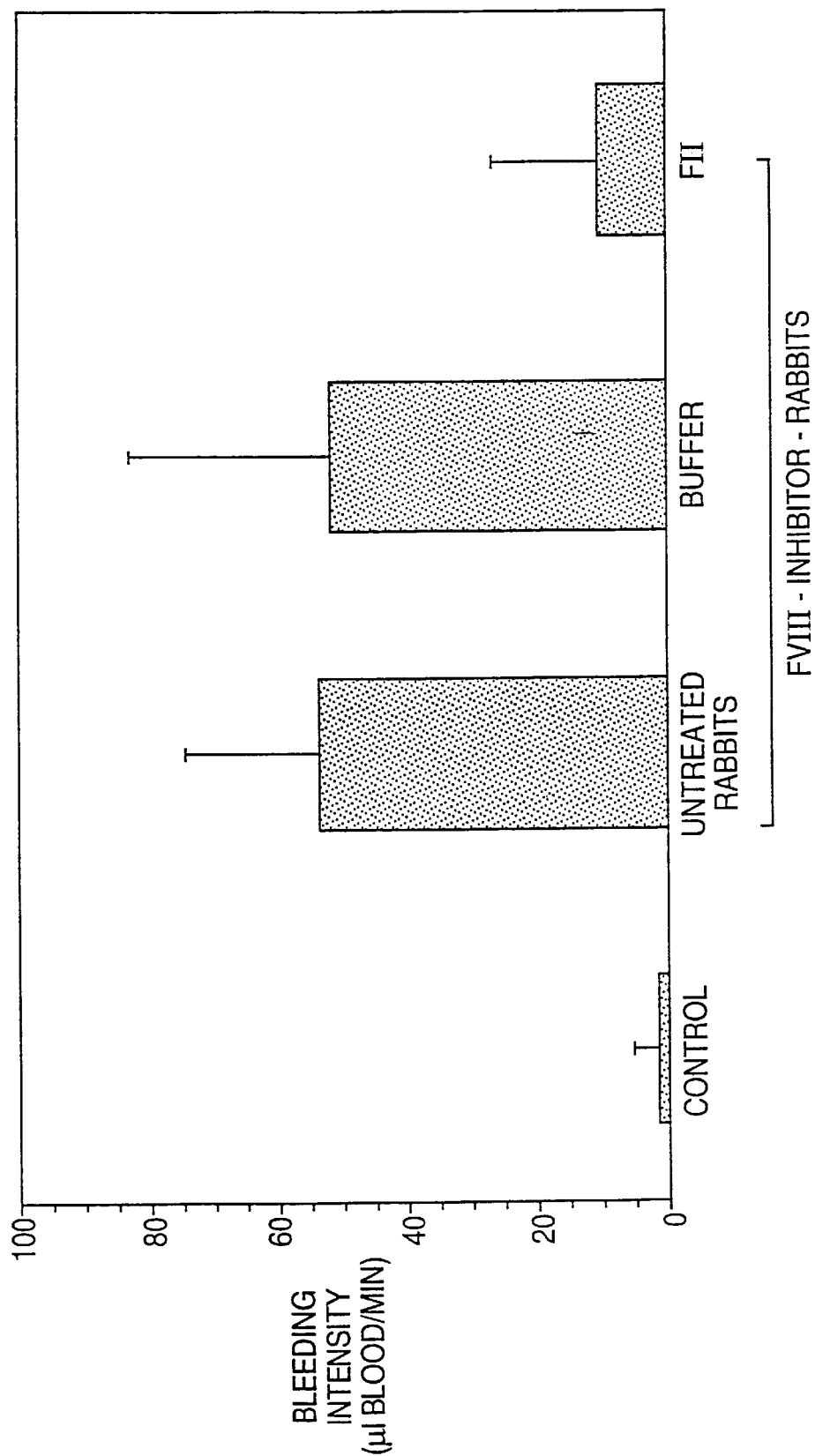
FIG. 6 shows the in vivo effect of a factor II preparation on factor VIII inhibitor rabbits.

To test the in vivo efficacy of the preparation according to the invention, a factor VIII inhibitor hemophilia rabbit model was used. White New Zealand rabbits weighing approximately 2 kg each were anesthesized. After the onset of anesthesia, each right femoral vein was prepared and a permanent venous access was established. Through the latter, per kg body weight, 0.5 ml of a human factor VIII inhibitor plasma (1500 BU/ml) were infused during 10 min. 30 min after the end of infusion, the bleeding characteristic was determined by using a modified method according to Giles et al., Blood 60:727–730 (1982). For this, the fur surrounding the claw of a hind paw of the rabbit was shaved to prevent blood emerging at the later bleeding from being absorbed by the fur. The nail cuticle was injured by means of a nail clipper; immediately thereafter, filters were placed therebelow such that the blood could drip directly onto the filter without being sucked up thereby on account of a capillary effect, so as to prevent a forming blood clot from being destroyed. The filter units were exchanged every 2 minutes, and the emerging blood was collected in fractions. Blood was continued to be collected for 30 minutes, and then the wound was cauterized if the bleeding had not stopped. To quantitate the bleeding characteristic, the filters were each extracted with 0.04% ammonium hydroxide solution for 5 h, whereby the erythrocites, which had been collected in the filter with the blood, were lysed. By a 10 min sonication, the hemoglobin was extracted and quantitated photometrically at 416 nm against a calibration curve. The latter was established by pipetting rabbit blood in volumes of between 10 $\mu$l and 1 ml onto filters, extracting the filters as described above and photometrically determining the hemoglobin at 416 nm. The bleeding characteristics of the nail cutting was determined by graphically plotting the amounts of blood per 2 min fraction against time. For an evaluation, the accumulated blood loss was determined by graphically plotting the volume of the individual blood fractions against time. The slope of the cumulative bleeding between 10 and 20 min was taken as a relevant bleeding criterion. This value was independent of the initial blood amount which was subject to variations from rabbit to rabbit, depending on the claw cut. The increase of the bleeding characteristic in 10 to 20 min observation intervals served as a measure for the intensity of bleeding. An increase equal zero meant that the bleeding had stopped, an increase >0 with a correlation coefficient of >0.8 meant that there was a constant bleeding. Under the test conditions, healthy rabbits had a bleeding intensity of <2 $\mu$l blood/min. Factor VIII inhibitor rabbits exhibited a bleeding intensity of approximately 50 $\mu$l blood/min (cf. FIG. 6). Factor VIII inhibitor rabbits which had been treated with a factor II preparation according to Example 3 at a dosage of 75 U/kg body weight as an infusion over 30 min showed a mean (n=6) bleeding intensity of 9.3 $\mu$l/min and thus a significant reduction as compared to the untreated inhibitor animal.

EXAMPLE 15

In vivo effect in case of von Willebrand factor/factor VIII inhibitor

Figure 7:
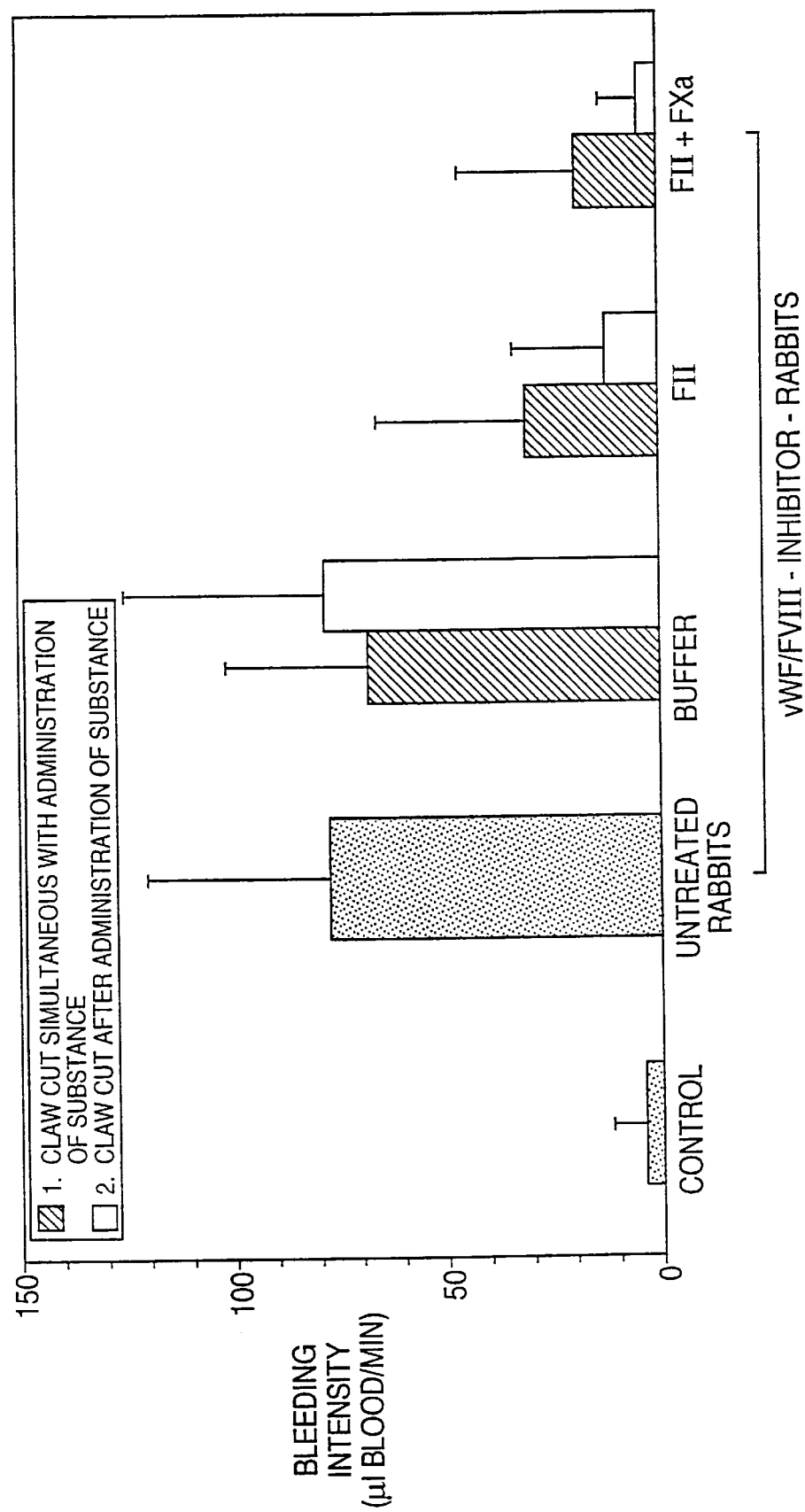

Analogous to Example 14, a von Willebrand factor/factor VIII inhibitor model was established by infusing rabbits with an anti-von Willebrand factor/factor VIII antiplasma from goat which had been recovered by immunization of goats with a purified factor VIII/von Willebrand factor preparation, at a dosage of 1 ml/kg body weight. Such pre-treated animals exhibited an increased intensity of bleeding (cf. FIG. 7). The bleeding characteristics were measured by claw cuts performed on these animals, simultaneously with an infusion of the test substance and 30 min after infusion of the test substance had ended. By administering factor II as a bolus of 2.5 ml at a dosage of 75 U/kg, the initially increased bleeding intensity could be reduced from 77 $\mu$l/min to 31 $\mu$l/min (1st claw cutting) and 12 $\mu$l/min (2nd claw cutting), respectively. By combining-factor II (75 U/kg) with a factor Xab (prepared according to Example 4) at a dosage of 0.55 U/kg as a bolus, at an injection volume of 2.5 ml, the propensity to bleeding could be reduced from the initial value to 18 $\mu$l/min at the first claw cutting and 5 $\mu$l/min at the 2nd claw cutting. Thus, the abnormally increased bleeding behavior of the inhibitor animals was normalilzed to the level of the healthy control animals (4 $\mu$l/min).

In addition, also the combination of factor II (75 U/kg), factor Xa (0.55 U/kg) and antithrombin III (IMMUNO Vienna) (75 mU/kg) was examined in the same model. At the first claw cut, a reduction to 35 $\mu$l/min, and at the second claw cut, to 7 $\mu$l/min could be achieved (cf. FIG. 8). The addition of antithrombin III should prevent a generation of thrombin from prothrombin due to the enzyme factor Xa in the administered solution.

EXAMPLE 16

Thrombogenicity of the preparation according to the invention

The individual components and mixtures thereof, of the preparation according to the invention were tested for their thrombogenic activity by using the method described by Wessler, J. Appl. Phys. 14:943–946 (1959) in the venous blood subject to stasis in rabbits.

Rabbits were anesthesized with pentobarbital, the vena jugularis of the animals was dissected and provided with loose ligatures at a distance of 1–2 cm. The substances to be tested were injected into the animals, into the ear vein opposite the dissected vena jugularis. The injection was effected within 15 seconds. After a waiting time of 10–15 seconds, the vein segment was clamped. After further 10 minutes, the clamped vein segment was removed and cut open in a citrated buffer in a Petri dish, and the thrombi obtained were evaluated between 0 and 4 by means of a score (cf. table)

| Degree of Thrombosis | Score |
| --- | --- |
| no formation of thrombi | 0 |
| few small thrombi | 0.5–1 |
| few middle-sized and many small thrombi | 2 |
| many middle-sized thrombi | 3 |
| few large thrombi | 3.5 |
| one coherent thrombus | 4 |

Each substance was tested on six animals each receiving 75 U of factor II/kg, 0.55 U of factor Xa/kg and 75 mU of antithrombin III/kg either separately or in combination. The following table shows the mean value of the Wessler score of six examined animals each. Pure citrated buffer which was also used as a dilution buffer was used as the control.

| Test Substance | | | |
|---|---|---|---|
| Factor II | Factor Xa | Antithrombin III | Wessler Score |
| + | − | − | 0.17 |
| − | + | − | 0.17 |
| − | − | + | 0.08 |
| + | + | − | 0.25 |
| + | − | + | 0.08 |
| − | + | + | 0.17 |
| + | + | + | 0.17 |
| − | − | − | 0.2 |
| (Bufer) | (Buffer) | (Buffer) | |

It proved that none of the components used, neither separately nor in combination, had a thrombogenic activity in rabbit.

EXAMPLE 17

Action of the preparation according to the invention in dependence on the form of administration A preparation according to Example 6 which contained factor II and factor Xa was each tested for its efficacy in 6 rabbits with induced factor VIII inhibitor hemophilia (cf. Example 14). The dose examined was as described in Example 15. As the control, the animals were infused with pure buffer.

In the first test, an infusion of the test substances was carried out for 30 minutes, corresponding to approximately 15 min/kg body weight, by means of an automatic infusion pump, at an infusion rate of 1 ml/min. In a second test, the same dose, yet given as a bolus within 30 seconds in a small injection volume of 2.5 ml/kg body weight was administered to the animals. As in Example 14, the bleeding intensity was measured during and after substance administration. It proved that both, at slow infusion with a large infusion volume, and also at rapid injection of a small volume dose, but with identical doses relative to the body weight, the pathologically extended bleeding intensity of 67 μl/min could be normalized to 5 μl/min, which corresponds to the bleeding behavior of the healthy control animals. By administration of buffer no change of the bleeding intensity was found with either of the two infusion modalities. Despite the rapid injection as a bolus, no intolerance reaction could be observed during injection, and neither so during slow infusion. For commercially available preparations of comparable indication (activated prothrombin complex preparations), infusion rates in the range of <0.05 ml/min/kg body weight are recommended to avoid acute thromboembolic side effects and intolerance reactions. As the test indicated, due to its high purity the preparation of the invention could be administered without any side effects at 5 ml/min/kg body weight, i.e. at the 100-fold injection rate.

EXAMPLE 18

Action of partial prothrombinase in rats exhibiting a platelet defect

Fawn-Hooded rats described by T. B. Tschopp and M. B. Zucker (Hereditary Defect in Platelet Function in Rates, Blood 1972; 40:217–226) are used as the thrombocytopathy model. This rat strain which had been further characterized by S. L. Raymond and W. J. Dodds (Characterization of the Fawn-Hooded Rats as a Model for Hemostatic Studies, Thrombos Diathes. haemorrh. 1975; 33:361–369) is characterized by an abnormally increased bleeding time and a reduced platelet aggregation, while prothrombin time, partial thromboplastin time, plasma factor VIII and fibrinogen levels as well as platelet number are in the same range as that of the healthy rat. The thrombopathy occurring in the fawn-hooded rat is associated with a reduced thrombin-induced ATP and ADP release, as well as with a reduced serotonin release and thus is characterized as "storage pool deficiency" reflecting the "storage pool deficiency" in man.

The fawn-hooded rats are anesthesized with ketamine-xylazine (100 mg/kg+5 mg/kg) i.m. A catheter is placed into a jugular vein, via which the substances to be tested are infused. Subsequently, the bleeding time is determined, Simplate R disposable blood lancet (Organon, Technica) being used therefor. At a distance of approximately 1.5 cm from the radix of the tail, one dorsal, and subsequently one ventral longitudinal section are made and the bleeding time is measured. The mean value of the two individual measurements is taken as the bleeding time. Then the test substance (buffer, factor II according to Example 2, factor Xa according to Example 4, and partial prothrombinase according to Example 6) is applied; after 30 minutes, the bleeding time is determined again. Healthy Sprague-Dawley rats (Charles River) are used as control.

Testing was effected in groups of 10 animals each, the complex of the partial prothrombinase being administered in 2 doses, 75 U/kg body weight (BW) prothrombin and 0.55 U/kg BW factor Xa as well as 150 U/kg BW prothrombin and 1.1 U/kg BW factor Xa. As the control, the individual components and buffer are administered. The mean bleeding times measured in the individual test groups are given in the following table. Healthy rats have a bleeding time of 168±5 seconds under the same test conditions, while rates suffering from thrombopathy have an increased bleeding time of 335±10 seconds. By administering partial prothrombinase, this abnormally increased bleeding time can be reduced to approximately 270 seconds.

TABLE

| Bleeding time (sec) Mean value from | | Factor II (U/kg) | | |
|---|---|---|---|---|
| 10 animals | | 0 | 75 | 150 |
| FXa (U/kg) | 0 | 335 ± 10 | 296 ± 13$^{ns}$ | 307 ± 11$^{ns}$ |
| | 0.55 | n.d. | 273 ± 13* | n.d. |
| | 1.1 | 320 ± 13$^{ns}$ | n.d. | 268 ± 11*** |

Statistical evluation:
The data are given as mean values ± standard deviation. The group mean values were compared by means of the Student T test.

EXAMPLE 19

Action of partial prothrombinase in von Willebrand factor-deficient dog

A dog exhibiting congenital von Willebrand factor deficiency having non-measurable von Willebrand factor activity and antigen plasma levels and a factor VIII plasma concentration that is reduced by 50% is treated with a partial prothrombinase at a dose of 100 U/kg BW. For this, the dog is anesthesized and subsequently the partial prothrombinase, produced according to Example 6, is given intravenously as a bolus. Immediately before administration of the test substance as well as 15 min, 30 min, 1 h, 2 h, 3 h, 24 h and 48 h after infusion, blood samples are taken, plasma is produced therefrom, and the prothombin, thrombin and factor VIII concentrations are determined in the plasma samples.

Before administering the partial prothrombinase as well as 3 and 24 h after injection, the cuticle bleeding characteristics are determined. For this, the method of A. R. Giles, S. Tinlin and R. Greenwood, A Canine Model of Hemophilic (Factor VIII:C Deficiency) Bleeding, Blood 1982; 60, is used in a modified form. The fur surrounding the claw is shaved to prevent blood emerging at the later bleeding from being absorbed by the fur. The cuticle is injured by means of a nail clipper. Immediately thereafter, filters (Pipetman P5000 protection filter, Gilson) are established below the wound such that blood can drip directly onto the filter without being sucked up thereby on account of a capillary effect, so as to prevent a forming blood clot from being destroyed. The filter units are exchanged every 2 minutes, and the emerging blood is collected in fractions. Blood is continued to be collected for 30 minutes, and then the wound is cauterized if the bleeding has not stopped. Different claws of one and the same animal can be used.

To quantitate the bleeding characteristic, the blood collected in fractions on the filters is each extracted with 5 ml of a 0.04% ammonium hydroxide solution for 5 h. Thereby the erythrocites, which have been collected in the filter with the blood, are lysed. By a 10 min sonication (Sonorex RK 100, Bandelin electronic, Berlin), the hemoglobin is extracted and quantitated photometrically at 416 nm against a calibration curve. A calibration curve can be established by pipetting canine blood in volumes of between 10 $\mu$l and 1 ml onto filters, extracting the filters as described above and photometrically determining the hemoglobin at 416 nm. Correspondingly, linear calibration curves can be established which enable the hemoglobin concentration to be calculated directly for the amount of blood per filter. The bleeding characteristics of the cuticle cutting are determined by graphically plotting the amounts of blood per 2 min fraction against time. For an evaluation of the bleeding characteristics, the accumulated blood loss is determined by entering in the graph the individual blood fractions additively against time. The increase of the accumulated bleeding between 10 and 20 min is taken as a relevant bleeding criterion. This value is independent of the initial blood amount which may be subject to variations because of poorly standardizable claw cutting techniques. The increase of the bleeding characteristic in 10 to 20 min observation intervals serves as a measure for the intensity of bleeding and is stated in ml blood/min. An increase equal zero, corresponding to 0 ml/min, means that the bleeding has stopped; an increase >0 with a correlation coefficient of >0.8 means that there is a constant bleeding. Normal dogs tested under these conditions do not exhibit a bleeding in the observation interval, i.e. the bleeding has already previously come to a stop (bleeding intensity: 0.0 ml/min).

Prior to administration of the partial prothrombinase, the bleeding intensity was 1.05 ml/min, and after 3 h it was reduced to 0.35 ml/min, and after 24 h it was further reduced to 0.47 ml/min.

The factor VIII plasma level remained constant over the entire period of observation, von Willebrand factor antigen remained below the detection limit, prothrombin was at 0.7 U/ml before substance administration and rose to 2.4 U/ml after injection of the partial prothrombinase and was eliminated from circulation with a half-life of approximately 24 h. 1 h after administration of the test substance, a significant thrombin generation could be determined with a chromogenic substrate for thrombin Th1 (IMMUNO). Injection of partial prothrombinase was tolerated by the dog without any side effects.

EXAMPLE 20

Action of partial prothrombinase and of von Willebrand factor in the von Willebrand factor-deficient dog Analogous to Example 19, the dog was treated with a partial prothrombinase at a dosage of 100 U/kg BW and a purified von Willebrand factor at a dosage of 60 RCOF U/kg BW. Administration of this combination lead to a complete normalization of the abnormally increased bleeding behavior after 24 h in the von Willebrand factor-deficient dog, the plasma parameters being comparable as in Example 19 relative to prothrombin and thrombin. Therebeyond, there was an endogenous factor VIII increase to approximately 200% of the initial value, which remained constant over a period of more than 48 h and subsequently returned to the initial value over a period of approximtely 120 h. Von Willebrand factor was eliminated with a half-life of 20 h. From the literature (L. Drouet, J. Roussi, M. Bonneau, G. A. Pignaud, P. L. Turecek, F. Dorner, U. Schlokat, F. G. Falkner, B. Fischer, A. Mitterer and H. P. Schwarz, The effect of recombinant human von Willebrand Factor in pigs with severe von Willebrand Disease. Blood 1995; 86: 612a–AbsNo.2435 (abs)) it had been known that the administration of von Willebrand factor alone leads to an only partial normalization of the bleeding behavior.

EXAMPLE 21

Action of partial prothrombinase as an antagonist of peptide anticoagulants

A partial prothrombinase in a composition of 57 U of factor II and 1.2 U of factor Xa was dissolved in 20 mM Tris-HC1-buffer containing 150 mM NaCl, pH 7.4, and incubated for 15 min at room temperature for the formation of the complex. Subsequently, an aliquot of 50 $\mu$l was taken and incubated for 90 seconds at 37° C. with 50 $\mu$l of a Tris-imidazole buffer, pH 8.4. Subsequently, it was admixed with 100 $\mu$l of a solution of the chromogenic substrate methoxy-carbonyl-D-cyclohexyl alanyl-glycyl-L-arginine-p-nitroanilide-hydroacetate so that the concentration of the chromogenic substrate was 1 mmol/l. Subsequently, the kinetics of the cleavage of the chromogenic substrate was photometrically determined at 405 nm for 3 min at 37° C. The chromogenic substrate which is hydrolyzed by both thrombin and factor Xa, had a $\Delta$OD/min of 0.084 when incubated with partial prothrombinase. As a control, factor Xa of the same concentration, yet without prothrombin was used in this test, and there appeared a conversion rate of the chromogenic substrate of 0.064 $\Delta$OD/min. Recombinant hirudin (Rhein-Biotech) at a concentration of 0.0025 U/ml was added to the partial prothrombinase, and the conversion rate of the chromogenic susbtrate was also investigated. It showed that no further substrate conversion could be measured after the deduction of the substrate conversion of pure factor Xa (0.064 $\Delta$OD/min), which was due to a complete neutralisation of the hirudin.

Beside the effective and specific thrombin inhibitor hirudin, then also the selective factor Xa inhibitor, recombinant Tick-anticoagulant peptide, a recombinant equivalent of serin protease inhibitor of ornithodoros moubata whose anticoagulatory in vivo-efficacy had been described by G. P. Vlasuk, D. Ramjit, T. Fujita et al. in Comparison of the In Vivo Anticoagulant Properties of Standard Heparin and the Highly Selective Factor Xa Inhibitors Antistasin and Tick Anticoagulant Peptide (TAP) in a Rabbit Model of Venous Thrombosis. Thrombos Haemostas 1991; 65: 25W–262, was added at a concentration of 50 Fg/ml. Already 30 min after the addition of the recombinant tick-anticoagulant peptide, no enzyme activity could be measured any longer with the chromogenic substrate. The test shows that partial prothrombinase is an efficient antagonist of the peptide anticoagulants hirudin and tick-anticoagulant peptide.

What is claimed is:

1. A method of establishing a supranormal prothrombin concentration in vivo in the blood of a patient, wherein the method comprises administering an effective dose of purified prothrombinase factors to said patient, wherein said purified prothrombinase factors lack thrombin activity.

2. The method according to claim 1, wherein said administering further comprises administration of an effective dose of purified prothrombin.

3. The method according to claim 1, wherein said administering further comprises administration of an effective dose of purified prothrombin and purified factor Xa.

4. The method according to claim 1, wherein a supranormal concentration of at least 1.5 U of prothrombin/ml blood is established.

5. The method according to claim 1, wherein a supranormal concentration of at least 2 U of prothrombin/ml blood is established.

6. The method according to claim 1, wherein the purified prothrombinase factors are administered with a double double-chamber syringe.

7. The method according to claim 3, wherein the purified prothrombin and factor Xa are administered with a double double-chamber syringe.

8. The method according to claim 1, wherein the administering includes an effective dose of at least one of factor V or factor Va.

9. The method according to claim 1, wherein the administering does not include phospholipids.

10. The method according to claim 1, wherein the administering does not include any free calcium ions.

11. The method according to claim 10, wherein the administering further comprises administration of a calcium chelating agent.

12. The method according to claim 1, wherein the administering further comprises administration of magnesium ions.

13. The method according to claim 3, wherein the effective dose comprises factor $Xa\beta$.

* * * * *

UNITED STATES PATENT AND TRADEMARK OFFICE
CERTIFICATE OF CORRECTION

PATENT NO. : 6,039,945  
DATED : March 21, 2000  
INVENTOR(S) : Peter TURECEK et al.

Page 1 of 3

Figure 5A:
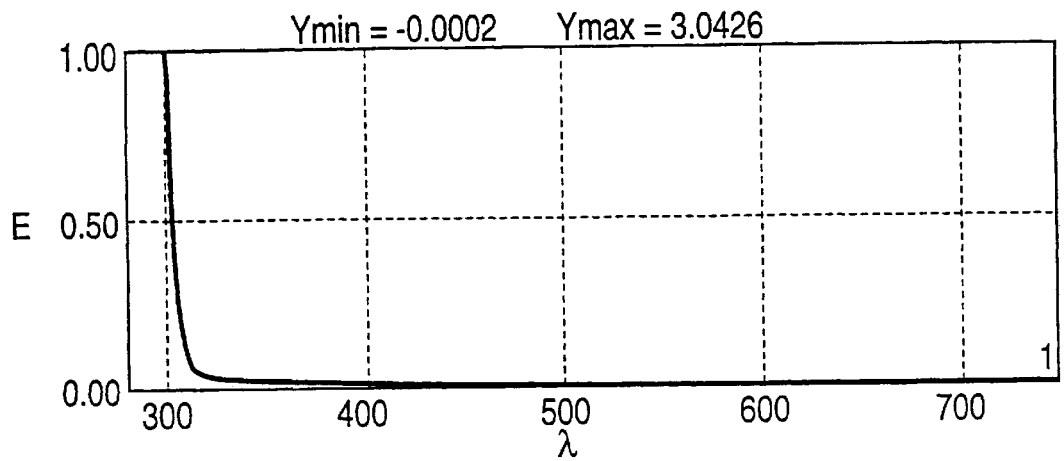
FIG. 5 shows the spectroscopic analysis of one example of the preparation (A) according to the invention as compared to standard preparations [activated prothrombin complex (B), prothrombin complex (C)]
Figure 5B:
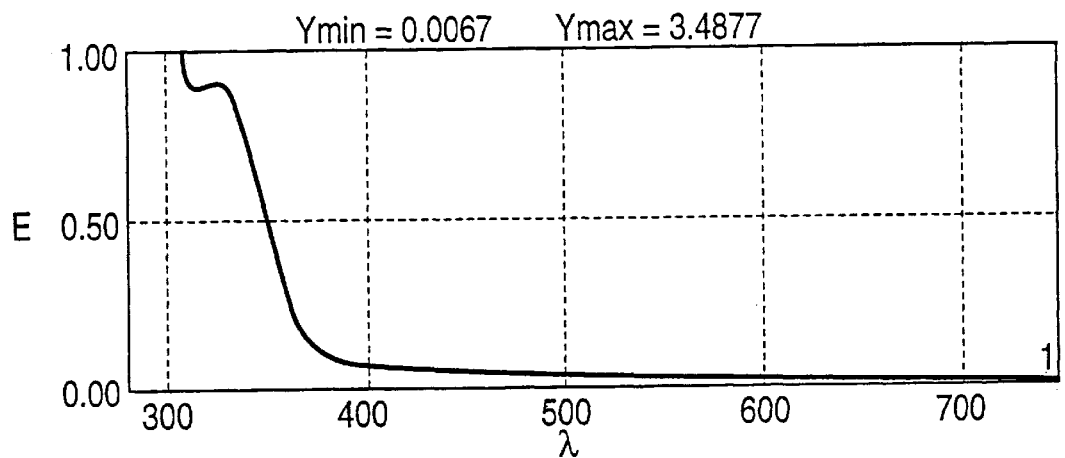
Figure 5C:
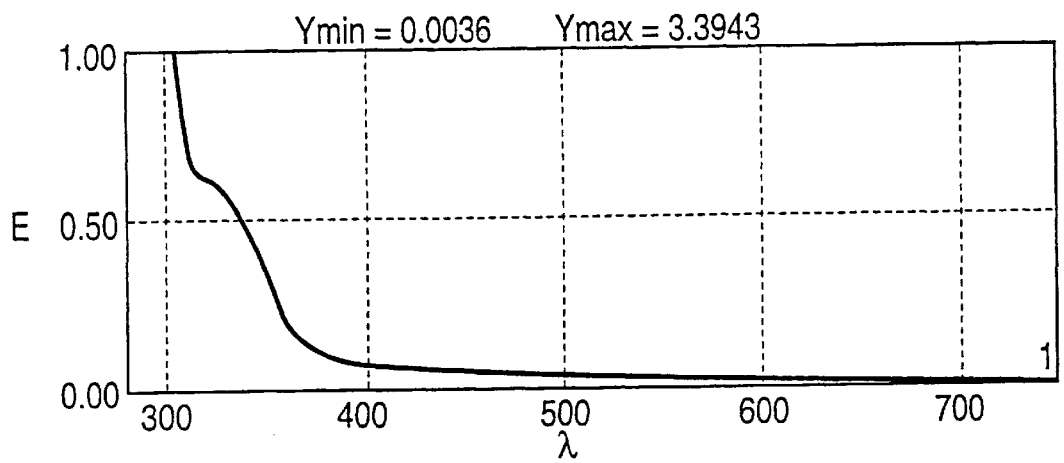

It is certified that error appears in the above-identified patent and that said Letters Patent is hereby corrected as shown below:

Column 3, line 13, after "preferably" insert --being present--;

Column 9, line 41, delete "dosis" and insert --dose--;

Column 9, line 43, delete "thrombisis" and insert --thrombosis--;

Column 12 delete lines 48-51 and insert --Figs. 5A-5C show the spectroscopic analysis of one example of the preparation (Fig. 5A) according to the invention as compared to standard preparations of activated prothrombin complex (Fig. 5B) or prothrombin complex (Fig.5C).--;

Column 14, line 42, delete "dissolvd" and insert --dissolved--;

Column 14, line 50, delete "Chormatography" and insert --chromatography--;

Column 14, line 53, delete "diamter" and insert --diameter--;

UNITED STATES PATENT AND TRADEMARK OFFICE
CERTIFICATE OF CORRECTION

PATENT NO. : 6,039,945
DATED : March 21, 2000
INVENTOR(S) : Peter TURECEK et al.

It is certified that error appears in the above-identified patent and that said Letters Patent is hereby corrected as shown below:

Column 3, line 13, after "preferably" insert --being present--;

Column 9, line 41, delete "dosis" and insert --dose--;

Column 9, line 43, delete "thrombisis" and insert --thrombosis--;

Column 12 delete lines 48-51 and insert --Figs. 5A-5C show the spectroscopic analysis of one example of the preparation (Fig. 5A) according to the invention as compared to standard preparations of activated prothrombin complex (Fig. 5B) or prothrombin complex (Fig.5C).--;

Column 14, line 42, delete "dissolvd" and insert --dissolved--;

Column 14, line 50, delete "Chormatography" and insert --chromatography--;

Column 14, line 53, delete "diamter" and insert --diameter--;

UNITED STATES PATENT AND TRADEMARK OFFICE
CERTIFICATE OF CORRECTION

PATENT NO. : 6,039,945
DATED : March 21, 2000
INVENTOR(S) : Peter TURECEK et al.

It is certified that error appears in the above-identified patent and that said Letters Patent is hereby corrected as shown below:

Column 21, line 19, delete "(Bufer)" and insert --(BUFFER)--;

Column 25, line 2, delete "25W" and insert --257--.

Signed and Sealed this

Fifth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.   : 6,039,945
DATED        : March 21, 2000
INVENTOR(S)  : Peter Turecek et al.

It is certified that error appears in the above-identified patent and that said Letters Patent is hereby corrected as shown below:

<u>Column 3,</u>
Line 13, after "preferably" insert -- being present --;

<u>Column 9,</u>
Line 41, delete "dosis" and insert -- dose --;
Line 43, delete "thrombisis" and insert -- thrombosis --;

<u>Column 12,</u>
Delete lines 48-51, and insert -- Figs. 5A-5C show the spectroscopic analysis of one example of the preparation (Fig. 5A) according to the invention as compared to standard preparations of activated prothrombin complex (Fig. 5B) or prothrombin complex (Fig.5C). --;

<u>Column 14,</u>
Line 42, delete "dissolvd" and insert -- dissolved --;
Line 50, delete "Chormatography" and insert -- chromatography --;
Line 53, delete "diamter" and insert -- diameter --;

<u>Column 15,</u>
Line 35, delete "DE 43 25 852" and insert -- DE 43 25 872 --

<u>Column 16,</u>
Line 20, delete "proove" and insert -- prove --;
Line 44, delete "at once" and insert -- by the addition of solvent --;

<u>Column 17,</u>
Line 40, delete "E" and insert -- A --;

<u>Column 18,</u>
Line 27, delete "specta" and insert -- spectra --;

<u>Column 20,</u>
Line 25, delete "normalilzed" and insert -- normalized --;

UNITED STATES PATENT AND TRADEMARK OFFICE
CERTIFICATE OF CORRECTION

PATENT NO. : 6,039,945
DATED : March 21, 2000
INVENTOR(S) : Peter Turecek et al.

It is certified that error appears in the above-identified patent and that said Letters Patent is hereby corrected as shown below:

Column 21,
Line 19, delete "(Bufer)" and insert -- (BUFFER) --;

Column 25,
Line 2, delete "25W" and insert -- 257 --.

This certificate supersedes Certificate of Correction issued June 5, 2001.

Signed and Sealed this

Twentieth Day of August, 2002

*Attest:*

JAMES E. ROGAN
*Attesting Officer*     *Director of the United States Patent and Trademark Office*